US011116830B2

(12) United States Patent
Price et al.

(10) Patent No.: US 11,116,830 B2
(45) Date of Patent: Sep. 14, 2021

(54) BACTERIAL POLYSACCHARIDE-CONJUGATED CARRIER PROTEINS AND USE THEREOF

(71) Applicant: THE UNITED STATES OF AMERICA, as represented by the Secretary, Department of Health and Human Services, Silver Spring, MD (US)

(72) Inventors: Gregory A. Price, Silver Spring, MD (US); Che-Hung Robert Lee, Silver Spring, MD (US); Margaret C. Bash, Silver Spring, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/954,161

(22) PCT Filed: Dec. 18, 2018

(86) PCT No.: PCT/US2018/066272
§ 371 (c)(1),
(2) Date: Jun. 15, 2020

(87) PCT Pub. No.: WO2019/126197
PCT Pub. Date: Jun. 27, 2019

(65) Prior Publication Data
US 2021/0154288 A1 May 27, 2021

Related U.S. Application Data

(60) Provisional application No. 62/607,066, filed on Dec. 18, 2017.

(51) Int. Cl.

*A61K 39/095* (2006.01)
*A61K 39/02* (2006.01)
*A61P 31/04* (2006.01)
*A61K 39/00* (2006.01)

(52) U.S. Cl.
CPC .......... *A61K 39/095* (2013.01); *A61K 39/107* (2013.01); *A61P 31/04* (2018.01); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS 9,173,931 B2 11/2015 Jessouroun et al.

FOREIGN PATENT DOCUMENTS

CN 107151270 A 9/2017

OTHER PUBLICATIONS

Beernink et al., "A meningococcal factor H binding protein mutant that eliminates factor H binding enhances protective antibody responses to vaccination," *The Journal of Immunology* 186(6): 3606-3614 (ePub Feb. 16, 2011).
Costa et al., "Human factor H (FH) impairs protective meningococcal anti-FHbp antibody responses and the antibodies enhance FH binding," *mBio* 5(5): e01625-14, 9 pages (Aug. 26, 2014).
Gockel and Russell, "Induction and recall of immune memory by mucosal immunization with a non-toxic recombinant enterotoxin-based chimeric protein," *Immunology* 116: 477486 (Oct. 25, 2005).
Hatic et al., "In vitro assembly of novel cholera toxin-like complexes," *Analytical Biochemistry* 292(2):171-177 (ePub Apr. 27, 2011).
International Search Report and Written Opinion from parent PCT Application No. PCT/US2018/066272 16 pages (dated Mar. 26, 2019).
Martin et al., "Recombinant antigen-enterotoxin A2/B chimeric mucosal immunogens differentially enhance antibody responses and B7-dependent costimulation of CD4 + T cells," *Infection and Immunity* 69(1): 252-261 (Jan. 1, 2001).
Price and Bash, "Development of an FHbp-CTB holotoxin-like chimera and the elicitation of bactericidal antibodies against serogroup B *Neisseria meningitidis*," *Vaccine* 36(5): 644-652 (Dec. 26, 2017).
Price and Bash, "Development of neisseria meningitidis factor H binding protein holotoxin-like chimeras," Poster, *American Society of Microbiology* (2015).
Price and Bash, "Immunogenicity of meningococcal factor H binding protein-cholera holotoxin-like chimeras in mice," Poster, *International Pathogenic Neisseria Conference* (Sep. 4, 2016 to Sep. 9, 2016).
Price and Holmes, "Evaluation of TcpF-A2-CTB chimera and evidence of additive protective efficacy of immunizing with TcpF and CTB in the suckling mouse model of cholera," *PLos one* 7(8): e442434, 11 pages (Aug. 7, 2012).

(Continued)

*Primary Examiner* — Padmavathi Baskar
(74) *Attorney, Agent, or Firm* — Klarquist Sparkman, LLP

(57) ABSTRACT

Immunogenic compositions that include a bacterial capsular polysaccharide conjugated to a carrier protein are described. In some embodiments, the bacterial capsular polysaccharide is a *Neisseria meningitidis* capsular polysaccharide. The carrier protein includes an *N. meningitidis* factor H binding protein (fHbp) linked to cholera toxin subunit B (CTB). Administration of the immunogenic compositions elicits an immune response that includes production of meningococcal polysaccharide-specific and fHbp-specific antibodies. Use of the immunogenic compositions as meningococcal vaccines is also described.

16 Claims, 16 Drawing Sheets

Specification includes a Sequence Listing.

(56) References Cited

OTHER PUBLICATIONS

Figure 1:
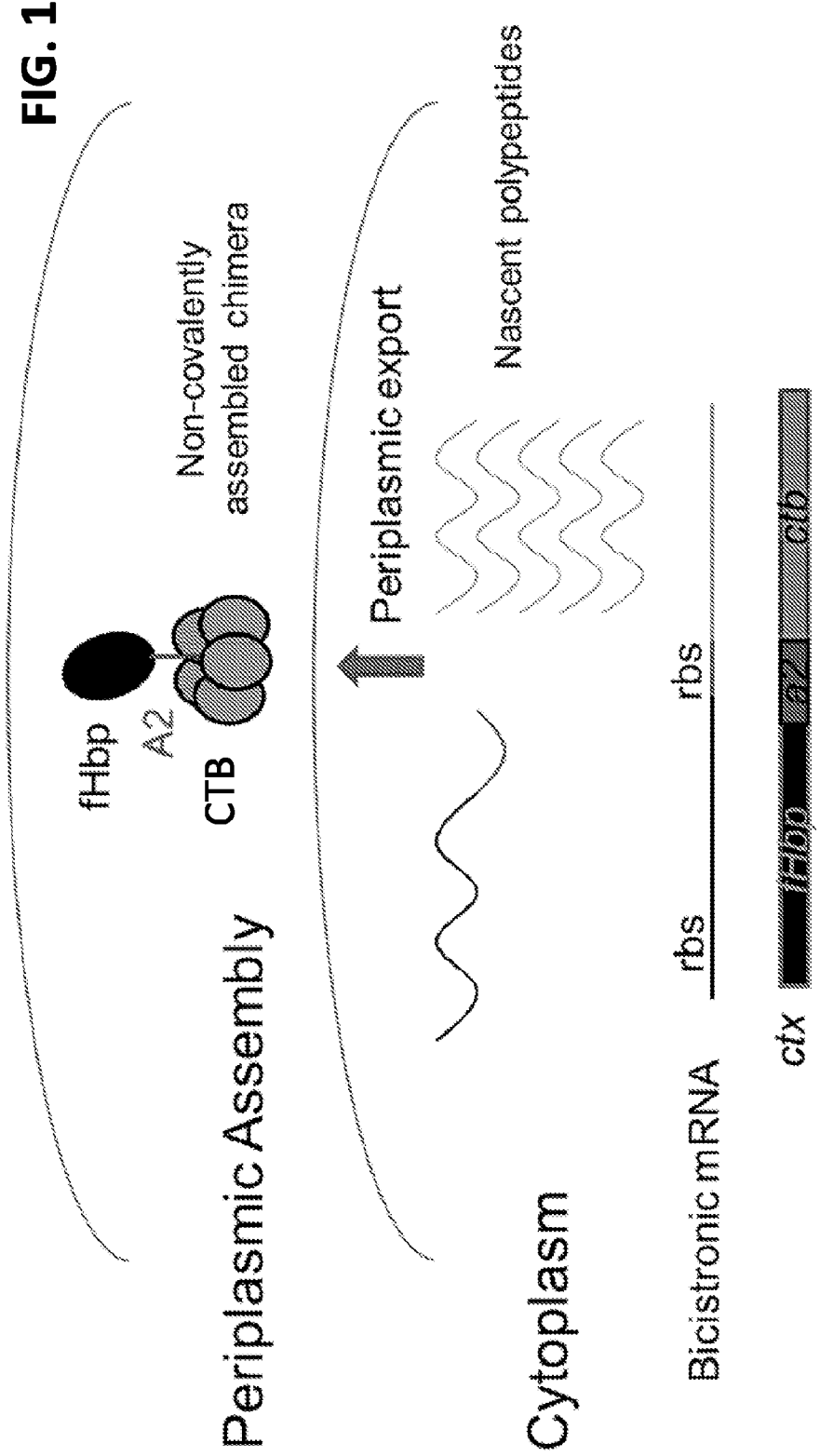

Price and Holmes, "Immunizing adult female mice with a TcpA-A2-CTB chimera provides a high level of protection for their pups in the infant mouse model of cholera," *PLos one* 8(12): e3356, 12 pages (Dec. 4, 2014).
Price et al., "Development of a meningococcal serogroup A Factor H binding protein glycoconjugate vaccine using cholera holotoxin-like chimeras," *Poster, International Pathogenic Neisseria Conference*, (Sep. 23-28, 2018).

Tinker et al., "Immunogenicity of a west nile virus DIII-cholera toxin A2/B chimera after intranasal delivery," *Toxins* 6(4): 1397-1418 (Apr. 22, 2014).

Zhao et al., "Characterization of antigen-presenting cells induced by intragastric immunization with recombinant chimeric immunogens constructed from *Streptococcus mutans* AgI/II and type I or type II heat-labile enterotoxins," *Molecular Oral Microbiology* 26(3): 200-209 (Mar. 31, 2011).

Zhao et al., "Identification and characterization of intestinal antigen-presenting cells involved in uptake and processing of a nontoxic recombinant chimeric mucosal immunogen based on cholera toxin using imaging flow cytometry," *Clinical and Vaccine Immunology* 21(1): 74-84 (e-pub Nov. 6, 2011).

FIG. 3C

G$_{M1}$ Ganglioside ELISA Human Serum Factor H Binding

1 ——— fHbp-CTB
2 ——— fHbpR41S-CTB
3 ——— CTB

FIG. 4A
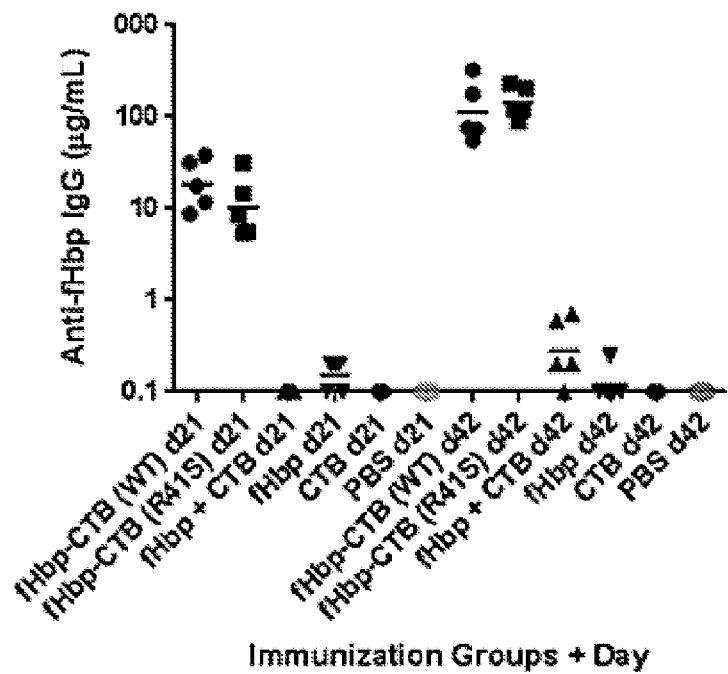
FIG. 4B Anti-CTB IgG Concentrations (day 21 or 42)
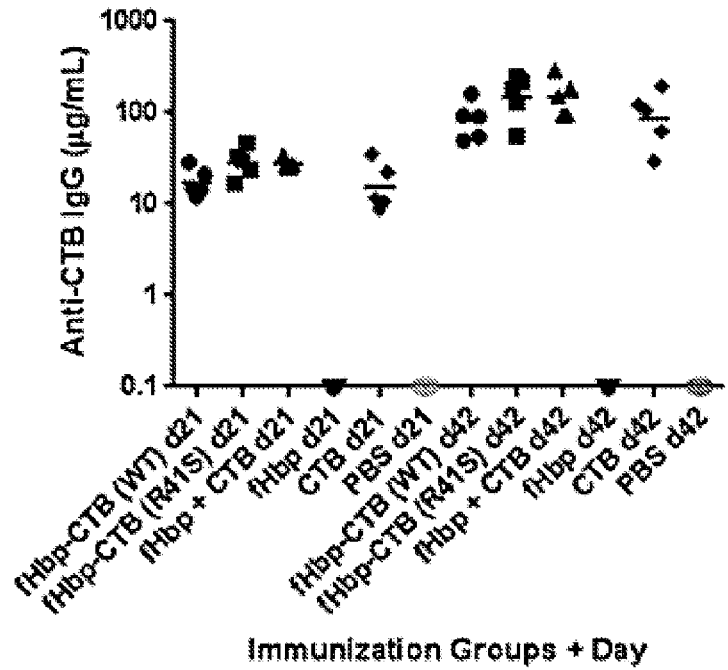

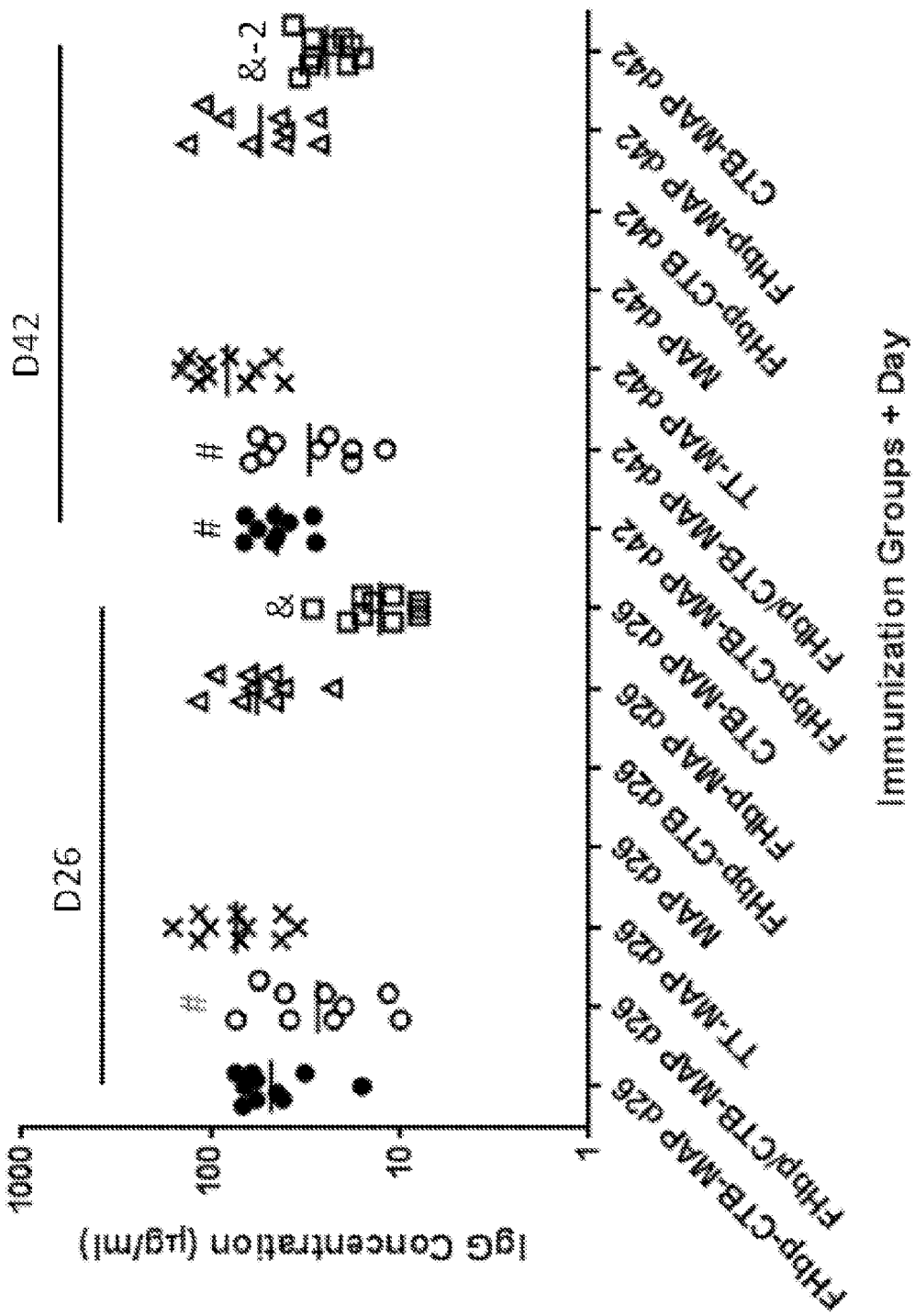

SEQUENCE LISTING

<160> NUMBER OF SEQ ID NOS: 9

<210> SEQ ID NO 1
<211> LENGTH: 274
<212> TYPE: PRT
<213> ORGANISM: Neisseria meningitidis

<400> SEQUENCE: 1

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 2
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 2

Leu Asp Glu Tyr Gln Ser Lys Val Lys Arg Gln Ile Phe Ser Gly Tyr
1               5                   10                  15

Gln Ser Asp Ile Asp Thr His Asn Arg Ile Lys Asp Glu Leu
            20                  25                  30

```
<210> SEQ ID NO 3
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 3

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 4
acttggccac aggtgcgggg cttgccgatg c                              31

<210> SEQ ID NO 5
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 5
ttgcggccgc ttgcttggcg gcaaggccga tatg                           34

<210> SEQ ID NO 6
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 6
gctggatcag tccgtcagca aaaacgagaa actgaagctg g                   41

<210> SEQ ID NO 7
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 7
ccagcttcag tttctcgttt ttgctgacgg actgatccag c                   41
```

-continued

```
<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 8
atcatatggg tgcggggctt gccgatgc                                    28

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 9
attcactcga gttgcttggc ggcaaggccg atatg                            35
```

BACTERIAL POLYSACCHARIDE-CONJUGATED CARRIER PROTEINS AND USE THEREOF

CROSS REFERENCE TO RELATED APPLICATION

This is a § 371 U.S. national stage of International Application No. PCT/US2018/066272, filed Dec. 18, 2018, which claims the benefit of U.S. Provisional Application No. 62/607,066, filed Dec. 18, 2017, which is herein incorporated by reference in its entirety.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, 9531-101679-03_Sequence_Listing.txt, Jun. 12, 2020, 5.24 KB, which is incorporated by reference herein. In the accompanying sequence listing:

FIELD

This disclosure concerns factor H binding protein (fHbp)-based immunogenic compositions conjugated to a polysaccharide and methods of using the compositions, such as in the prevention of bacterial infections, such as, but not limited to, a meningococcal infection.

BACKGROUND

The *Neisseria meningitidis* factor H binding protein (fHbp) is a lipidated outer membrane protein and an important meningococcal virulence factor contained in both serogroup B meningococcal vaccines approved for use in the United States (Seib K L, *Expert Rev Vaccines*, 14, 841-59, 2015). fHbp plays a critical role in serum resistance by binding to the human complement regulatory protein factor H (hfH) and downregulating the complement cascade (Madico G, *J Immunol*, 177, 501-10, 2006) (Schneider M C, *J Immunol*, 176, 7566-75, 2006). Studies have demonstrated knocking out fHbp expression can eliminate complement resistance of *N. meningitidis* (Madico G, *J Immunol*, 177, 501-10, 2006) (Seib K L, *Infect Immun.*, 77, 292-92009). Because of its importance as a meningococcal virulence factor and its ability to elicit protective immune responses in animal studies, fHbp was developed as a vaccine antigen and is a component of both food and drug administration (FDA)-approved Meningococcal Group B (MenB) vaccines (Seib K L, *Expert Rev Vaccines*, 14, 841-59, 2015) (Fletcher L D, *Infect Immun.*, 72, 2088-100, 2004) (Masignani V, *J Exp Med.*, 197, 789-99, 2003) (McNeil L K, *Microbiol Mol Biol Rev.*, 77, 234-52, 2013). fHbp is antigenically variable and is divided into two distinct subfamilies (A and B) based on amino acid sequence homology. Generally, antibodies elicited to subfamily A are not protective against strains expressing subfamily B, and vice versa. Sequence types are divided into three variant groups (var1, var2, and var3), or two subfamilies (A and B) (Fletcher L D, *Infect Immun.*, 72, 2088-100, 2004) (Masignani V, *J Exp Med.*, 197, 789-99, 2003). Subfamily A corresponds to var2 and var3, and subfamily B corresponds to var1. Unique sequences within a subfamily or variant group are given an identifying number. Immunization with fHbp can elicit cross-protective bactericidal antibodies to strains expressing fHbp within the same subfamily (Fletcher L D, *Infect Immun.*, 72, 2088-100, 2004) (Masignani V, *J Exp Med.*, 197, 789-99, 2003) (Jiang H Q, *Vaccine*, 28, 6086-93, 2010) (Seib K L, *Infect Immun.*, 79, 970-81, 2011). There is cross-reactivity between var2 and var3, but not between var1 and the other two variant groups, which is consistent with the data for the subfamilies (Masignani V, *J Exp Med.*, 197, 789-99, 2003) (Seib K L, *Infect Immun.*, 79, 970-81, 2011). In the USA, MenB strains expressing subfamily B are more common (59%) than subfamily A (41%) (Wang X, *Vaccine.*, 4739-44, 2011).

Two MenB vaccines have been approved for use in individuals 10 through 25 years of age in the United States (Gandhi A, *Postgrad Med.*, 128, 548-56, 2016) (Mameli C, *Future Microbiol.*, 10, 1579-98, 2015). One vaccine, BEXERO® (4CMenB), contains three components in addition to recombinant fHbp: recombinant neisserial adhesion A (NadA), recombinant neisserial heparin binding protein (NHBP), and outer membrane vesicles (OMV) from strain NZ98/254, which include porin protein PorA (serosubtype P1.4) (Mameli C, *Future Microbiol.*, 10, 1579-98, 2015). fHbp (var1.1) is an important component of 4CMenB as adsorption of anti-fHbp IgG from human immune sera significantly reduces bactericidal titers against strains expressing homologous and heterologous fHbp (Rossi R, *Clin Vaccine Immunol.*, 22, 1227-34, 2015) (Vu D M, *Vaccine.*, 29, 1968-73, 2011). The other FDA-approved vaccine, TRUMENBA® (rLP2086), contains two lipidated recombinant fHbp antigens, one from subfamily A and one from subfamily B (Donald R G, *Hum Vaccin Immunother*, 1-11, 2016). In clinical studies, both vaccines elicited bactericidal antibodies against selected MenB strains measured with the human complement serum bactericidal activity (hSBA) assay (Donald, *Hum Vaccin Immunother*, 1-11, 2016) (O'Ryan M, *Drugs*, 74, 15-30, 2014).

Although fHbp has been demonstrated to be an important protective antigen, the extent to which fHbp interacts with fH upon immunization, and whether any fHbp-fH interaction affects the overall immunogenicity of fHbp in humans is currently unknown. Studies in hfH transgenic mice and infant rhesus macaques, the latter having a polymorphism in the fH gene that allows for either high or low binding to fHbp (Konar M, *PLoS One.*, 10, e0135996, 2015), have demonstrated that binding of fH to fHbp lowers the immunogenicity of fHbp (Beernink P T, *J Immunol.*, 186, 3606-14, 2011) (Costa I, 2014) (Giuntini S, *Vaccine*, 33, 7168-75, 2015) (Granoff D M, *J. Infect. Dis.*, 212, 784-92, 2015) (Rossi R, *Vaccine*, 31, 5451-7, 2013). Furthermore, 10 distinct human anti-fHbp antibody fragments (Fabs), and affinity purified fHbp-specific antibodies obtained from individuals immunized with fHbp were relatively ineffective at blocking fH binding to the surface of MenB (Beernink, *MBio.*, 6, e00842, 2015). Although these antibodies were bactericidal, a study suggests a potential fHbp-fH interaction that skews the antibody repertoire to epitopes outside of the fHbp-fH binding pocket (Beernink, *MBio.*, 6, e00842, 2015). Subsequently, studies in both hfH transgenic mice and rhesus macaques demonstrated that mutations within fHbp can significantly reduce fHbp-fH binding and are more immunogenic and elicit greater bactericidal killing (Costa I, 2014) (Rossi R, *Vaccine*, 31, 5451-7, 2013) (Granoff D M, *JCI Insight*, 1, e88907, 2016). Modifications of FHbp systems that improve immunogenicity and expand its utility as a conjugate vaccine component are needed.

SUMMARY

Factor H binding protein (fHbp) has been used for conjugation of capsular polysaccharide (Pinto V, PLos ONE 8(11):e79304). However, in these systems, while the fHbp served as a carrier protein, the fHbp specific bactericidal responses generated were low titer. Disclosed herein are immunogenic compositions that ca be used to prevent and treat bacterial infections, and that produce high bactericidal responses.

Immunogenic compositions for preventing or treating bacterial infection and transmission are described. The disclosed compositions include a meningococcal capsular polysaccharide conjugated to a carrier protein that includes a *Neisseria* (*N.*) *meningitidis* fHbp. In some non-limiting examples, the composition includes a *N. meningitidis* capsular polysaccharide, and can be used to induce an immune response to *Neisseria*, such as *N. meningitidis*.

Provided herein are immunogenic compositions that include a bacterial capsular polysaccharide, such as, but not limited to a *N. meningitidis* capsular polysaccharide, conjugated to a protein. In some embodiments, the protein includes a *N. meningitidis* fHbp fused to a linking domain, and a cholera toxin subunit B (CTB), wherein the fHbp-linking domain fusion is covalently or non-covalently linked to CTB. In some examples, the linking domain is a cholera toxin subunit A2 domain. In a specific non-limiting example, the fHbp-linking domain fusion is non-covalently linked to CTB.

Also provided are methods of inducing an immune response to bacteria, such as, but not limited to, *Neisseria*, in a subject by administering to the subject an effective amount of an immunogenic composition disclosed herein.

The foregoing and other objects, features, and advantages of the disclosure will become more apparent from the following detailed description, which proceeds with reference to the accompanying figures.

BRIEF DESCRIPTION OF THE DRAWINGS

FIG. 1 is a schematic representation of fHbp-A2-CTB expression in *E. coli.*

FIG. 2 shows SDS-PAGE and gel filtration analysis of purified fHbp-CTB and fHbpR41S-CTB chimeras. fHbp-CTB and fHbpR41S-CTB chimeric proteins were boiled and reduced prior to separation on a 4-15% SDS-PAGE gel causing the CTB pentamer to disassemble into monomers (~11.5 kDa) and separate from fHbp-A2 (~30 kDa).

FIGS. 3A-3C are graphs showing the results of GM1 ganglioside ELISAs, which demonstrate fHbp-CTB and fHbpR41S-CTB chimeric protein assembly. (FIGS. 3A-3B) Equimolar concentrations of fHbp-CTB, fHbpR41S-CTB, CTB, and rfHbp were loaded into 96-well plates coated with GM1 ganglioside and serially diluted. Following washing, the plates were probed with either rabbit anti-CT antibody (FIG. 3A) or a mouse fHbp-specific monoclonal antibody Jar 4 (FIG. 3B), followed by a second probing with a goat anti-rabbit or anti-mouse HRP-conjugated antibody. The 96-well plates were then developed at 490 nm and the optical densities were recorded. (FIG. 3C) Fixed concentrations of equimolar amounts of antigen were added to a $G_{M1}$ ganglioside-coated plate. Following washing, human serum was added to the plate and serially diluted. The plates were then probed with a polyclonal mouse anti-human factor H antibody, followed by an HRP-conjugated goat anti-mouse antibody. The plates were developed at 490 nm and the optical densities were recorded.

FIGS. 4A-4B are graphs showing the concentration of serum anti-fHbp and anti-CTB IgG determined using quantitative ELISA. (FIG. 4A) Serum anti-fHbp antibody concentrations measured at days 21 and 42. On both days, the antibody concentrations measured in the fHbp-CTB and fHbpR41S-CTB groups were significantly higher than the other groups measured on the same day (P<0.0001). (FIG. 4B) Serum anti-CTB antibody concentrations measured at days 21 and 42. Statistical differences were determined using ANOVA with the Tukey-Kramer post-test analysis.

FIG. 5 is a graph showing hSBA titers against a panel of fHbp variant 1/subfamily B strains. Pooled sera were heat-inactivated and assayed for bactericidal activity using human complement against a panel of variant 1 or subfamily B fHbp-expressing strains. Titers were determined as the lowest reciprocal dilution that gave ≥50% killing versus complement control wells. Negative controls were pooled sera samples from both the CTB and PBS immunized mice.

FIG. 6 is a graph of day 42 anti-fHbp IgG concentration measured against fHbp B24 antigen.

FIG. 7 is a graph of day 42 anti-fHbp IgG concentration against fHbp subfamily A05 as measured by quantitative ELISA.

FIG. 8 is a graph showing bactericidal activity of pooled mouse sera against five B24 meningococcal strains.

FIG. 9 is a graph showing bactericidal activity of pooled mouse sera against four various fHbp subfamily B expressing meningococcal strains.

FIG. 10 is a graph showing bactericidal activity of pooled mouse sera against seven various fHbp subfamily A expressing meningococcal strains.

FIG. 11 is a schematic showing the reductive amination chemistry used for conjugation of MenA polysaccharide (PS) to FHbp-A2-CTB.

FIGS. 12A-12C are graphs showing the results of quantitative ELISAs performed on day 26 sera to measure antibodies against fHbp (FIG. 12A), MAP (FIG. 12B) and CTB (FIG. 12C).

FIGS. 13A-13B are graphs showing anti-MAP IgG concentrations (FIG. 13A) and anti-FHbp IgG concentrations (FIG. 13B) in sera 42 days following immunization of mice with the indicated carrier proteins with or without MAP.

FIGS. 14A-14B are graphs showing bactericidal titers of chimeric proteins and conjugates against four MenB strains (FIG. 14A) and one MenA strain (FIG. 14B).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, Dec. 14, 2018 5.20 KB, which is incorporated by reference herein. In the accompanying sequence listing:

```
SEQ ID NO: 1 is the amino acid sequence of
fHbp from N. meningitidis strain CU385.

MNRTAFCCLS LTTALILTAC SSGGGGVAAD

IGAGLADALT APLDHKDKGL QSLTLDQSVRKNEKLKLAAQ

GAEKTYGNGD SLNTGKLKND KVSRFDFIRQ IEVDGQLITL

ESGEFQVYKQSHSALTAFQT EQIQDSEHSG KMVAKRQFRI

GDIAGEHTSF DKLPEGGRAT YRGTAFGSDDAGGKLTYTID

FAAKQGNGKI EHLKSPELNV DLAAADIKPD GKRHAVISGS

VLYNQAEKGSYSLGIFGGKA QEVAGSAEVK TVNGIRHIGL

AAKQ

SEQ ID NO: 2 is an amino acid sequence of
the cholera toxin subunit A2 domain.
LDEYQSKVKRQIFSGYQSDIDTHNRIKDEL SEQ ID NO: 3 is an amino acid sequence of
the cholera toxin subunit B.
TPQNITDLCAEYHNTQIHTLNDKIFSYTESLAGKREMAIITFKNG

ATFQVEVPGSQHIDSQKKAIERMKDTLRIAYLTEAKVEKLCVWNN

KTPHAIAAISMAN

SEQ ID NOs: 4-9 are primer sequences.
```

DETAILED DESCRIPTION

I. Abbreviations

CTB cholera toxin B
ELISA enzyme-linked immunosorbent assay
fHbp factor H binding protein
hSBA human complement serum bactericidal activity
MAP Meningococcal serogroup A polysaccharide
MenA Meningococcal Group A
MenB Meningococcal Group B
PS polysaccharide
TT tetanus toxoid

II. Terms and Methods

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the term "comprises" means "includes." Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. In one example the adjuvant is one or more toll-like receptor (TLR) agonists, such as an agonist of TLR1/2 (which can be a synthetic ligand) (for example, Pam3Cys), TLR2 (for example, CFA, Pam2Cys), TLR3 (for example, polyI:C, poly A:U), TLR4 (for example, MPLA, Lipid A, and LPS), TLR5 (for example, flagellin), TLR7 (for example, gardiquimod, imiquimod, loxoribine, Resiquimod®), TLR7/8 (for example, R0848), TLR8 (for example, imidazoquionolines, ssPolyU, 3M-012), TLR9 (for example, ODN 1826 (type B), ODN 2216 (type A), CpG oligonucleotides) and/or TLR11/12 (for example, profilin). In one example, the adjuvant is lipid A, such as lipid A monophosphoryl (MPL) from *Salmonella enterica* serotype Minnesota Re 595 (for example, Sigma Aldrich Catalog #L6895). Administration: The introduction of a composition into a subject by a chosen route.

Administration can be local or systemic. For example, if the chosen route is intranasal, the composition is administered by introducing the composition into the nasal passages of the subject. Similarly, if the chosen route is intramuscular, the composition is administered by introducing the composition into a muscle of the subject. If the chosen route is oral, the composition is administered by introducing the subject ingesting the composition. Exemplary routes of administration of use in the methods disclosed herein include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of an amino acid in a polypeptide with one or more different amino acids. In the context of a protein sequence, an amino acid substitution is also referred to as a mutation.

Capsular polysaccharide: A type of polysaccharide found in the capsule layer on the surface of bacteria. The capsular polysaccharide can be a Meningococcal polysaccharide, *Streptococcus pneumonia* polysaccharide, *Haemophilus influenzae* polysaccharide, *Salmonella typhi* polysaccharide, Group B *Streptococcus agalactiae* polysaccharide, or any combination thereof. Bacterial polysaccharides are disclosed, for example, in U.S. Pat. No. 9,173,931, incorporated herein by reference. In the context of the present disclosure, the capsular polysaccharide is from one or more serogroups of *N. meningitidis*, such as any of serogroup A, serogroup B, serogroup C, serogroup D, serogroup X, serogroup Y, serogroup Z, serogroup 29E or serogroup W135.

Cholera toxin: A protein complex secreted by the bacterium *Vibrio cholera*. Cholera toxin includes two subunits— the A subunit (CTA) and the B subunit (CTB). CTA is responsible for the toxic effects of cholera toxin, while CTB mediates delivery of CTA to target cells. CTB is a 55 kDa homopentameric, non-toxic protein that binds to the GM1 ganglioside on mammalian cells. CTA is 28 kDa and includes two primary domains—A1 and A2. The A1 domain possess toxic activity and the A2 domain anchors CTA into the CTB subunit.

Effective amount: An amount of agent, such as an immunogen (such as a meningococcal polysaccharide-conjugated carrier protein), that is sufficient to elicit a desired response, such as an immune response in a subject. It is understood that to obtain a protective immune response against an organism of interest (such as *N. meningitidis*) can require multiple administrations of a disclosed immunogen, and/or administration of a disclosed immunogen as the "prime" in a prime boost protocol wherein the boost immunogen can be different from the prime immunogen. Accordingly, an effective amount of a disclosed immunogen can be the amount of the immunogen sufficient to elicit a priming immune response in a subject that can be subsequently boosted with the same or a different immunogen to elicit a protective immune response.

In one example, a desired response is to inhibit or reduce or prevent a *Neisseria meningitidis* infection. The *N. meningitidis* infection does not need to be completely eliminated or reduced or prevented for the method to be effective. For example, administration of an effective amount of the agent can decrease the *N. meningitidis* infection (for example, as measured by bacteria number or by number or percentage of subjects infected by *N. meningitidis*) by a desired amount, for example by at least 50%, at least 60%, at least 70%, at least 80%, at least 90%, at least 95%, at least 98%, or even at least 100%, as compared to a suitable control.

Factor H binding protein (fHbp): A naturally lipidated, 27 kDa outer membrane protein of *N. meningitidis* that is important for the survival of the bacterium in human blood. fHbp is a component of two licensed vaccines (BEXSERO® and TRUMENBA®) against meningococcal serotype B. One exemplary fHbp amino acid sequence is the fHbp sequence of strain *N. meningitidis* CU385, set forth herein as SEQ ID NO: 1.

Heterologous: A heterologous protein or nucleic acid refers to a protein or nucleic acid derived from a different source, strain, or species.

Immune response: A response of a cell of the immune system, such as a B cell, T cell, macrophage or polymorphonucleocyte, to a stimulus such as an antigen/immunogen or vaccine. In some embodiments, the response is specific for a particular antigen(s) (an "antigen-specific response"). An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses include, for example, measuring proliferation and/or activity of lymphocytes (such as B or T cells), secretion of cytokines or chemokines, inflammation, antibody production and the like. In some embodiments, the response is a B cell response, and results in the production of specific antibodies (such as MenA-specific antibodies and/or fHbp-specific antibodies). A "protective immune response" is an immune response that confers protection against a disease caused by *N. meningitidis*, such as serogroup A, B, C, Y or W135. A "therapeutic immune response" treats an existing infection with *Neisseria*. In some embodiments, the subject has a *N. meningitidis* infection, and administration of the immunogenic composition increases clearance of the *Neisseria meningitidis*.

Immunize: To render a subject (such as a mammal) protected from an infectious disease (for example, *N. meningitidis* infection), such as by vaccination.

Immunogen: A compound, composition, or substance (for example, a meningococcal polysaccharide-conjugated carrier protein, such as fHbp-A2-CTB) that can elicit an immune response in an animal, including compositions that are injected or absorbed into an animal. Administration of an immunogen to a subject can lead to immunity against a pathogen of interest, such as *Neisseria meningitidis*. An "immunogenic composition" is a composition that includes at least one immunogen.

Inhibiting or treating a disease: Inhibiting the full development of a disease or condition, for example, in a subject who is at risk for a disease such as a *N. meningitidis* infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. Inhibiting a disease can include preventing or reducing the risk of the disease, such as preventing or reducing the risk of bacterial infection. The beneficial effect can be evidenced, for example, by a delayed onset of clinical symptoms of the disease in a susceptible subject, a reduction in severity of some or all clinical symptoms of the disease, a slower progression of the disease, a reduction in the bacterial load, an improvement in the overall health or well-being of the subject, or by other parameters that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated or purified away from other biological components, such as other biological components in which the component naturally occurs, such as other chromosomal and extrachromosomal DNA, RNA, membranes, cells and proteins. Biological components that have been "isolated" include those purified by standard purification methods. Isolated does not require absolute purity, and can include components that are at least 50% isolated, such as at least 75%, 80%, 90%, 95%, 98%, 99%, or even 99.9% isolated from other components.

Linked: Joined together or bonded by either covalent or non-covalent means.

Modification: A change in a nucleic acid or protein sequence. For example, sequence modifications include, for example, substitutions, insertions and deletions, or combinations thereof. For proteins, insertions include amino and/or carboxyl terminal fusions as well as intrasequence insertions of single or multiple amino acid residues. Insertions for nucleic acid sequence include 5' or 3' additions or intrasequence insertions of single or multiple nucleotides. Deletions are characterized by the removal of one or more amino acid residues from a protein sequence or one or more nucleotides from a nucleic acid sequence. Substitutional modifications are those in which at least one amino acid residue or nucleotide has been removed and a different residue or nucleotide inserted in its place. Substitutions, deletions, insertions or any combination thereof may be combined to arrive at a final mutant sequence. Protein modifications can be prepared by modification of nucleotides in the DNA encoding the protein, thereby producing DNA encoding the modification. Techniques for making insertion, deletion and substitution mutations at predetermined sites in DNA or RNA having a known sequence are well known in the art. A "modified" protein or nucleic acid is one that has one or more modifications as outlined above.

*Neisseria meningitidis*: A Gram-negative bacterium that causes meningitis and other forms of meningococcal disease.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residues is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence.

Sequence identity: The similarity between amino acid sequences is expressed in terms of the similarity between the sequences, otherwise referred to as sequence identity. Sequence identity is frequently measured in terms of percentage identity; the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. In the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Variants of a polypeptide are typically characterized by possession of at least about 75%, for example, at least about 80%, 85%, 90%, 91%, 92%, 93%, 94%, 95%, 96%, 97%, 98% or 99% sequence identity counted over the full-length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet.

As used herein, reference to "at least 90% identity" (or similar language) refers to "at least 90%, at least 91%, at least 92%, at least 93%, at least 94%, at least 95%, at least 96%, at least 97%, at least 98%, at least 99%, or even 100% identity" to a specified reference sequence.

Serogroup: Classification, such as of *Neisseria meningitidis* by virtue of immunologically detectable variations in the capsular polysaccharide. About 12 serogroups are known: A, B, C, X, Y, Z, 29-E, W-135, H, I, K, and L. Any one serogroup can encompass multiple serotypes and multiple serosubtypes. A serotype is a classification of *Neisseria meningitidis* strains based on monoclonal antibody-defined antigenic differences in the outer membrane protein porin PorB, or upon VR typing of amino acid sequences deduced from DNA sequencing. A single serotype can be found in multiple serogroups and multiple serosubtypes. "Serosubtype" is classification of *Neisseria meningitidis* strains based on antibody-defined antigenic variations on the outer membrane protein porin PorA, or upon VR typing of amino acid sequences deduced from DNA sequencing (Sacchi et al., 2000, *J. Infect. Dis.* 182:1169; see also the Multi Locus Sequence Typing web site). Most variability between PorA proteins occurs in two (loops I and IV) of eight putative, surface-exposed loops. The variable loops I and IV have been designated VR1 and VR2, respectively. A single serosubtype can be found in multiple serogroups and multiple serotypes.

Subject: Living multi-cellular vertebrate organisms, a category that includes human and non-human mammals. In an example, a subject is a human. In an additional example, a subject is selected that is in need of inhibiting of a *Neisseria* infection. For example, the subject is either uninfected and at risk for infection, or is infected in need of treatment.

Synthetic: Produced by artificial means in a laboratory, for example a synthetic nucleic acid or protein can be chemically synthesized in a laboratory.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen, such as *Neisseria meningitidis* capsular polysaccharide-conjugated to a carrier protein. Vaccines can elicit both prophylactic (preventative or protective) and therapeutic responses. Methods of administration vary according to the vaccine, but may include inoculation, ingestion, inhalation, or other forms of administration. Vaccines may be administered with an adjuvant to boost the immune response. In one specific, non-limiting example, a vaccine prevents and/or reduces the severity of the symptoms associated with *Neisseria* infection and/or decreases the viral load compared to a control.

III. Overview of Embodiments

Disclosed herein as an immunogenic composition that includes a bacterial capsular polysaccharide conjugated to a protein, wherein the protein comprises: a *N. meningitidis* factor H binding protein (fHbp); fused to a linking domain; and a cholera toxin subunit B (CTB), wherein the fHbp is covalently or non-covalently linked to the CTB. In some embodiments, the capsular polysaccharide is a Meningococcal polysaccharide, a *Streptococcus pneumonia* polysaccharide, a *Haemophilus influenzae* polysaccharide, a *Salmonnella typhi* polysaccharide, a Group B *Streptococcus agalactiae* polysaccharide, an *Escherichia coli* or any combination thereof. In a specific non-limiting example, the fHbp-linking domain is non-covalently linked to CTB.

In specific non-limiting examples, the capsular polysaccharide is a *Neisseria* (*N.*) *meningitidis* polysaccharide. In other non-limiting examples, the capsular polysaccharide comprises a *N. meningitidis* serogroup A, serogroup B, serogroup C, serogroup D, serogroup X, serogroup Y, serogroup Z, serogroup 29E or serogroup W capsular polysaccharide, or any combination thereof. In one of these non-limiting examples, the capsular polysaccharide is a *N. meningitidis* serogroup A capsular polysaccharide.

In some embodiments, the amino acid sequence of the fHbp is at least about 80% identical to SEQ ID NO: 1, such as at least about 90% identical to SEQ ID NO: 1, or at least about 95% identical to SEQ ID NO: 1. In another non-limiting example, the amino acid sequence of the fHbp comprises SEQ ID NO: 1.

In additional embodiments, the linking domain comprises a cholera toxin subunit A2 domain. In further embodiments, the amino acid sequence of the A2 domain is at least about 80% identical to SEQ ID NO: 2, such as at least about 90% identical to SEQ ID NO: 2, or at least about 95% identical to SEQ ID NO: 2. In one non-limiting example, the amino acid sequence of the A2 domain comprises or consists of SEQ ID NO: 2.

In more embodiments, the amino acid sequence of the CTB is at least about 80% identical to SEQ ID NO: 3, such as at least about 90% identical to SEQ ID NO: 3, or at least about 95% identical to SEQ ID NO: 3. In one non-limiting example, the amino acid sequence of the CTB comprises or consists of SEQ ID NO: 3.

In some embodiments, the immunogenic composition can also include a pharmaceutically acceptable carrier and/or an adjuvant.

Methods are also provided for inducing an immune response to bacteria in a subject, by administering to the subject an effective amount of the immunogenic composition disclosed herein. In some embodiments, the bacteria is *Neisseria*. In some embodiments, the immune response is a protective immune response. In other embodiment, the immune response is a therapeutic response. The subject can be a human or a veterinary subject.

IV. Immunogens

In some embodiments, the present disclosure provides fHbp chimeric proteins that elicit an immunogenic response by eliciting antibodies that are bactericidal for a bacteria, such as a variant strains of *N. meningitidis*, and their methods of use. An expression system was developed in *Escherichia coli* using cholera holotoxin-like chimeric proteins as a vaccine platform. This approach utilizes cholera toxin B (CTB) as a receptor binding protein and adjuvant for the antigen fHbp from variant strains.

A. Factor H Binding Protein Holotoxin-Like Chimeric Protein

In some embodiments, a factor H binding protein holotoxin-like chimeric protein can be used in methods to induce an immune response against *Neisseria*. In particular aspects, the fHbp holotoxin-like chimeric protein comprises at least two domains. The first domain, when present, is a receptor binding domain. The receptor binding domain can aid the fHbp holotoxin-like chimera binding to its cognate receptor. An exemplary receptor binding domain includes, but is not limited to, the non-toxic binding domain of cholera toxin (CT), known as subunit B (CTB). CTB is the non-toxic binding domain of CT that forms a donut-like structure composed of the five B polypeptides associated by non-covalent interactions. CTB binds to the monosialosyl ganglioside $G_{M1}$ on host cells and facilitates entrance of the chimeric proteins comprising the toxin into cells.

Cholera toxin is an $AB_5$ toxin comprised of five identical B polypeptide subunits (CTB) and one catalytic A polypeptide (CTA). The non-toxic A2 domain of the CTA subunit comprises a non-toxic A domain that passes through the central pore of CTB, linking the A and B subunits together by non-covalent interactions, and it is amenable to biological manipulation and can be linked to an antigen domain.

In other embodiments, the receptor binding domain can comprise the B subunit of the non-toxic heat-labile enterotoxin (LTB).

The second domain, when present, is an antigen domain. In some embodiments, the antigen domain is an immunostimulatory polypeptide or peptide. In some embodiments, the antigen domain is a bacterial antigen, a viral antigen, a fungal antigen, or a parasitic antigen. An exemplary antigen domain includes, but is not limited to, the *N. meningitidis* factor H binding protein. While *N. meningitidis* strains of any capsular group may be used, or combinations thereof, *N. meningitidis* strains of capsular group B are of particular interest as sources from which nucleic acid sequences encoding fHbp and domains thereof are derived. An exemplary antigen domain described in the Examples herein is the fHbp protein obtained from the MenB *N. meningitidis* strain CU385 (subvariant 1.1 or B24). The fHbp can contain amino acid sequences that are at least 80%, at least 85%, at least 90%, at least 95%, at least 98%, at least 99%, or 100% identical to SEQ ID NO: 1. The fHbp can include at most 1, 2, 3, 4, or 5 amino acid substitutions in SEQ ID NO: 1.

Nucleic acids encoding fHbp polypeptides for use in construction of chimeric fHbps contemplated herein are known in the art. Exemplary fHbp polypeptides are described in, for example, WO 2004/048404; Masignani et al. 2003 *J Exp Med* 197:789-799; Fletcher et al. *Infect Immun* 2004 2088-2100; Welsch et al. *J Immunol* 2004 172:5606-5615; and WO 99/57280. Nucleic acid (and amino acid sequences) for fHbp variants and subvariants are also provided in GenBank Accession Nos.: AY548371 (AAT01290.1) (from *N. meningitidis* strain CU385); NC_003112, GeneID: 904318 (NCBI Ref. NP_274866) (from *N. meningitidis* strain MC58): AY548370 (AAT01289.1) (from *N. meningitidis* strain H44/76); AY548377 (AAS56920.1) (from *N. meningitidis* strain M4105); AY548376 (AAS56919.1) (from *N. meningitidis* strain M1390); AY548375 (AAS56918.1) (from *N. meningitidis* strain N98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83).

A third domain, when present, is a linking domain. The linking domain aids in linking the antigen domain and the receptor domain together. An exemplary linking domain is the enzymatic non-toxic A2 subunit of CT. The A2 subunit of CT is connected at its N-terminus to an fHbp, with the A2 subunit linking the fHbp antigen domain to the CTB subunit receptor binding domain through a non-covalent interaction.

B. Factor H Binding Protein Holotoxin-Like Chimera Production

Polynucleotides encoding the disclosed chimeric proteins are also provided. These polynucleotides include DNA, cDNA, and RNA sequences which encode the holotoxin-like chimeric protein. The genetic code can be used to construct a variety of functionally equivalent nucleic acids, such as nucleic acids that differ in sequence but which encode the same protein sequence.

Exemplary nucleic acids can be prepared by cloning techniques. Examples of appropriate cloning and sequencing techniques, and instructions sufficient to direct persons of skill through many cloning exercises are known (see, e.g. Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013).

Nucleic acids can also be prepared by amplification methods Amplification methods include polymerase chain reaction (PCR), the ligase chain reaction (LCR), the transcription-based amplification system (TAS), and the self-sustained sequence replication system (3SR). The polynucleotides encoding a disclosed peptide can include a recombinant DNA which is incorporated into a vector, into an autonomously replicating plasmid, or into the genomic DNA of a prokaryote and eukaryote, or which exists as a separate molecule (such as cDNA) independent of other sequences. The nucleotides can be ribonucleotides, deoxyribonucleotides, or modified forms of either nucleotide. The term includes single and double forms of DNA.

Polynucleotide sequences encoding a disclosed peptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signals for introns, maintenance of the correct reading frame of that gene to permit proper translation of mRNA, and stop codons.

DNA sequences encoding the disclosed peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect, and mammalian organisms. Methods of expressing DNA sequences having eukaryotic or viral sequences in prokaryotes are well known in the art. Non-limiting examples of suitable host cells include bacteria, archea, insect fungi (for example, yeast), plant and animal cells (for example, mammalian cells, such as human) Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Transformation of a host cell with recombinant DNA can be carried out by conventional techniques.

Modifications can be made to a nucleic acid encoding a disclosed peptide without diminishing its biological activity. Some modifications can be made to facilitate the cloning, expression, or incorporation of the peptide into a fusion protein. Non-limiting examples of such modifications include termination codons, a methionine added at the amino terminus to provide an initiation site, additional amino acids placed on either terminus to create conveniently located restriction sites, or additional amino acids (such as poly His) to aid in purification steps.

Prokaryotic cells can be engineered to express fHbp-CTB chimeric proteins by means readily known to the skilled artisan. In one aspect, *E. Coli* can be used to express fHbp-CTB chimeric proteins. A polynucleotide is constructed that includes the genes encoding fHbp-A2 and CTB and the vector is transfected into a population of *E. Coli* cells. The cells are then grown under conditions promoting expression of the fHbp-CTP by the *E. Coli* cells. Transfection is conducted via conventional means, some of which are disclosed in the Examples herein.

An exemplary vector includes, but is not limited to, the vector backbone pGAP22, which is a derivative of the vector pGAP22A2. pGAP22 and pGAP22A2 are identical in design and restriction sites, except pGAP22 contains a shortened A2 domain starting at amino acid 211 (Leu) of the cholera toxin A subunit. DNA sequencing can be used to confirm proper construction of the vector before transfection of *E. Coli* cells.

C. Conjugation of Capsular Polysaccharides to the Factor H Binding Protein Holotoxin-Like Chimeric Protein Provided herein are immunogenic compositions wherein a bacterial capsular polysaccharide is conjugated to at least one of the receptor binding domain, the antigen domain, or the linking domain of the chimeric protein. Methods are known in the art for conjugating a polysaccharide to a protein (Lee C H, *Vaccine*, 27, 726-32, 2009).

Bacterial capsular polysaccharides are disclosed, for example, in U.S. Pat. No. 9,173,931, incorporated herein by reference. Polysaccharides and oligosaccharides for use in preferred embodiments include pneumococcal polysaccharides of, for example, serotypes 1, 2, 3, 4, 5, 6B, 7F, 8, 9N, 9V, 10A, 11A, 12F, 14, 15B, 17F, 18C, 19A, 19F, 20, 22F, 23F and 33F; meningococcal polysaccharides of serotypes A, B, C, W135, and Y, *Haemophilus influenzae* type b polysaccharide polyribosylribitol phosphate, group B streptococcal polysaccharides of serotypes III and V and *Salmonella typhi* Vi polysaccharide. Other polysaccharides can be used from pneumococcal and group B streptococcal serotypes, and meningococcal serogroups, as are other T-independent polysaccharide antigens, for example, polysaccharides derived from group A *Streptococcus*, Staphylococci, Enterococci, *Klebsiella pneumoniae, E. coli, Pseudomonas aeruginosa*, and *Bacillus anthracis*. In some embodiments, the polysaccharides are from Gram negative bacteria. In other embodiment, the polysaccharides are from Gram positive bacteria. Polysaccharides with side chain phosphorus and/or backbone phosphorus are suitable for use. The capsular polysaccharide can be a Meningococcal polysaccharide, a *Streptococcus pneumonia* polysaccharide, a *Haemophilus influenzae* polysaccharide, a *Salmonnella typhi* polysaccharide, a Group B *Streptococcus agalactiae* polysaccharide, an *Escherichia coli* polysaccharide, polysaccharides from group A *Streptococcus, Staphylococci, Enterococci, Klebsiella pneumoniae, E. coli, Pseudomonas aeruginosa*, and *Bacillus anthracis* or any combination thereof.

The bacterial capsular polysaccharide can be an *N. meningitidis* capsular polysaccharide. Meningococcal serogroup A polysaccharide (about 300 kDa) is composed of N-acetyl mannosamine 6-phosphate repeating units with α (1→phosphate) glycosidic linkage and about 70-90 percent O-acetylation at C3. Meningococcal serogroup W135 polysaccharide (~300,000 Daltons) is composed of (2→6) α-D-galactose (1→4) α-D-sialic acid repeating units with about 70 percent O-acetylation at C7 or C9 of the sialic acid residue.

In another aspect, the capsular polysaccharide derived from *N. meningitidis* serogroup A (MAP) may be substituted with capsular polysaccharide derived from *N. meningitidis* serogroups B, C, D, X, Y, Z, 29E, W-135, or a combination thereof. *N. meningitidis* serogroups A, B, C, D, X, Y, Z, 29E, and W-135 account for almost all cases of disease. Such conjugates can be administered to a subject capable of inducing an immune response to an antigen in order to provide protection against infection of these serogroups. Meningococcal serogroup Y polysaccharide (about 300 kDa) is composed of (2→6) α-D-galactose (1→4) α-D-sialic acid repeating units with about 70 percent O-acetylation at C7 or C9 of the sialic acid residue.

In some embodiments, the size of the *N. meningitidis* capsular polysaccharide for use in the disclosed compositions is about 200 to about 350 kDa, such as about 250 to about 300 kDa, although other sizes are contemplated, provided that the selected size of the polysaccharide is effective to induce production of antibodies in a subject after conjugation to a carrier protein. Conjugation methods are known in the art, and are disclosed, for example, in U.S. Pat. No. 9,173,931, incorporated herein by reference.

In some embodiments, a polysaccharide with side chain phosphorus and/or backbone phosphorus is utilized. In some non-limiting examples, the polysaccharide is subjected to an "activation" step which is a chemical treatment of the polysaccharide to provide chemical groups capable of reacting with the protein. The activation can involve functionalization of the polysaccharide with hydrazide groups that are reacted with aldehyde groups on a functionalized protein. Alternatively, the polysaccharide can be functionalized with aldehyde groups, ketone groups, or cyanate groups that are reacted with hydrazide groups on a functionalized protein.

Any suitable functionalization reaction can be employed to activate the polysaccharide with hydrazide groups. In some embodiments, reductive amination is utilized, wherein the polysaccharide is reacted with $NaIO_4$ in a periodate activation reaction to yield aldehyde groups, which are then reacted with adipic acid dihydrazide, followed by subsequent reduction with $NaBH_4$.

Any suitable functionalization reaction can be employed to activate the polysaccharide with aldehyde groups. Certain polysaccharides possess terminal aldehyde groups that can participate in the conjugation reaction. If the polysaccharide is activated with aldehyde groups, an oxidizing agent can be used, such as $NaIO_4$. Oxidizing agents have the potential for fragmenting the polysaccharide. Undesirable fragmentation can be avoided or controlled through selection of the particular oxidizing agent and the concentration of the oxidizing agent employed. Ketone groups are also capable of reacting with hydrazide, so activated of the polysaccharide with ketone groups can be employed in certain embodiments.

A strongly buffered (at pH of from about 6.5 to about 8, with a high buffer concentration of from about 100 mM to about 200 mM) activated polysaccharide solution can be employed in the conjugation reaction in the form of a strongly buffered solution. Any suitable buffer can be employed, such as, but not limited to, N-(2-Hydroxyethyl) piperazine-N'-(2-ethanesulfonic acid).

Conjugates can be prepared via the reaction of aldehyde and hydrazide groups (reductive amination). The reductive amination conjugation reaction can be employed to conjugate a hydrazide-modified reactant (protein or polysaccharide) to the other component containing aldehyde groups, see U.S. Pat. No. 9,173,931, incorporated by reference.

A conjugate can be purified by any suitable method. Purification is employed to remove unreacted polysaccharide, protein, or small molecule reaction byproducts. Purification methods of use include ultrafiltration, size exclusion chromatography, density gradient centrifugation, hydrophobic interaction chromatography, ammonium sulfate fractionation, and the like, as are known in the art. Alternatively, no purification may be necessary, or only a minor degree of purification can be desirable. The conjugate can be concentrated or diluted, or processed into any suitable form for use in pharmaceutical compositions V. Methods of Inducing an Immune Response An immunogenic composition comprising a capsular polysaccharide conjugated to a carrier protein (such as fHbp-A2-CTB) as disclosed herein can be administered to a subject to induce an immune response to treat or prevent a bacterial infection. In some embodiments, the bacterial infection is a *Streptococcus*, Staphylococci, Enterococci, *Klebsiella pneumoniae, E. coli, Pseudomonas aeruginosa*, or *Bacillus anthracis* infection. In other embodiments, the infection is a meningococcal infection. In some non-limiting examples, the subject is human. In other non-limiting examples, the subject is a veterinary subject. The immune response can be a protective immune response, for example, a response that inhibits subsequent infection with the bacteria, such as *N. meningitidis*. A subject can be selected for immunization that has, or is at risk for developing, infection or illness associated with bacteria. In some embodiments, the infection is a meningococcal infection, and the subject can be at risk, for example, because of exposure or the possibility of exposure to *N. meningitidis*.

Typical subjects intended for administration of the immunogenic composition include humans, as well as non-human primates and other animals. To identify relevant subjects, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods to detect and/or characterize a meningococcal infection. These and other routine methods allow the clinician to select patients in need of therapy. In accordance with these methods and principles, the immunogenic composition can be administered according to the teachings herein, or other conventional methods, as an independent prophylaxis or treatment program, or as a follow-up, adjunct or coordinate treatment regimen to other treatments.

The immunogenic composition is provided to the subject in an amount effective to induce or enhance an immune response against bacteria, such as, but not limited to, *Streptococcus, Staphylococci, Enterococci, Klebsiella pneumoniae, E. coli, Pseudomonas aeruginosa, Bacillus anthracis*, or *Neissearia*, in the subject, such as a human. In a specific non-limiting example, the immunogenic composition is provided to the subject in an amount effective to induce or enhance an immune response against *N. meningitidis*. The actual dosage of the immunogenic composition will vary according to factors such as the disease indication and particular status of the subject (for example, the subject's age, size, fitness, extent of symptoms, susceptibility factors, and the like), time and route of administration, other drugs or treatments being administered concurrently, as well as specific pharmacology of the composition for eliciting the desired activity or biological response in a subject. Dosage regimens can be adjusted to provide an optimum prophylactic or therapeutic response.

An immunogenic composition disclosed herein can be used in coordinate vaccination protocols or combinatorial formulations. There can be several boosts, and each boost can be the same or a different immunogen. In some examples, the boost can be the same immunogen as another boost, or the prime. The prime and boost can be administered as a single dose or multiple doses, for example two doses, three doses, four doses, five doses, six doses or more can be administered to a subject over days, weeks, or months. Multiple boosts can also be given, such one to five (for example, 1, 2, 3, 4, or 5 boosts), or more. Different dosages can be used in a series of sequential immunizations. For example, a relatively large dose in a primary immunization and then a boost with relatively smaller doses.

In some embodiments, the boost can be administered about 2, about 3, or about 4 weeks following the prime, or about several months after the prime. In some embodiments, the boost can be administered about 5, about 6, about 7, about 8, about 10, about 12, about 18, or about 24 months after the prime, or more or less time after the prime. Periodic additional boosts can also be used at appropriate time points to enhance the subject's "immune memory." The adequacy of the vaccination parameters chosen, such as formulation, dose, regimen and the like, can be determined by taking aliquots of serum from the subject and assaying antibody titers during the immunization program. In addition, the clinical condition of the subject can be monitored for the desired effect, for example inhibition of meningococcal infection (for example, *Neisseria meningitidis*) or improvement in disease state. If such monitoring indicates that vaccination is sub-optimal, the subject can be boosted with an additional dose of immunogenic composition, and the vaccination parameters can be modified in a manner expected to potentiate the immune response.

In some embodiments, the prime-boost method can include a protein-boost vaccination protocol to a subject. The method can include two or more administrations of the protein. The amount utilized in an immunogenic composition is selected based on the subject population (such as infant or elderly). An optimal amount for a particular composition can be ascertained by standard studies involving observation of antibody titers and other responses in subjects. It is understood that an effective amount of a disclosed immunogenic composition can include an amount that is ineffective at eliciting an immune response by administration of a single dose, but that is effective upon administration of multiple dosages, for example in a prime-boost administration protocol.

Upon administration of the immunogenic composition, the immune system of the subject typically responds to the immunogenic composition by producing antibodies specific for the antigen. Such a response signifies that an immunologically effective dose was delivered to the subject.

Infections, such as a meningococcal infection does not need to be completely eliminated or reduced or prevented for the methods to be effective. For example, elicitation of the immune response can prevent, reduce or inhibit infection with bacteria, such as *N. meningitidis*, by a desired amount, for example, by at least 10%, at least 20%, at least 50%, at least 60%, at least 70%, at least 80%, at least 90%, at least 95%, at least 98%, or even at least 100% (elimination or prevention of detectable infected cells), as compared to infection with the bacteria, such as *N. meningitidis*, in the absence of the immunization.

In some embodiments, the fHbp component and/or the capsular polysaccharide component of the immunogen induces and/or elicits an immune response in an animal. Generally, the immune response against the immunogen is protective (for example, prevents a disease in the animal). In some embodiments, the animal is a mammal. In some embodiments, the mammal is a human In some embodiments, the immunogen compositions disclosed herein induce and/or elicit a protective immune response in a subject against a bacterial infection, such as an *N. Meningitidis* infection. In some embodiments, the carrier protein fHbp-A2-CTB comprises one or more epitopes of fHbp.

The immunogenic compositions disclosed herein can be used in a method of inducing an immunogenic effect in a subject to prevent meningococcal infection, comprising administering a formulation comprising one or more capsular polysaccharides, wherein the capsular polysaccharides induce an immunogenic effect in an animal. The immunogenic effect can protect the animal in the event of meningococcus infection by inducing death of the bacterium.

In some embodiments, the method of inducing an immunogenic effect uses the natural non-covalent linking of antigens to the non-toxic cholera toxin B subunit (CTB) via the linking domain, the non-enzymatic cholera toxin A2 subunit that is connected to an antigen (Hajishengallis G, *J Immunol.*, 154, 4322-32, 1995) (Jobling M G, *Infect Immun.*, 60, 4915-24, 1992). CTB is a strong adjuvant and CTB adjuvanticity is enhanced if the antigen and CTB are physically coupled (Cholera, *Vaccines (Basel)*, 3, 579-96, 2015).

The following examples are provided to illustrate certain particular features and/or embodiments. These examples should not be construed to limit the disclosure to the particular features or embodiments described.

EXAMPLES

Example 1

This example describes a simple yet efficient method for recombinant production of soluble and immunogenic fHbp, In TRUMENBA®, lipidated fHbp is highly immunogenic, likely due to the ability of the lipid tail to stimulate the pattern recognition receptor TLR2 (Luo Y, *AAPS J.*, 18, 1562-75, 2016). However, expression of lipoproteins in *E. coli* can be challenging due to low protein expression and/or incomplete protein lipidation (Leng C H, *Expert Rev Vaccines.*, 14, 1623-32, 2015). The fHbp contained in BEXSERO® is an N-terminal fusion to GNA2091, a periplasmic lipoprotein that may stabilize fHbp and potentially increase fHbp immunogenicity (Bos, *J Biol Chem.*, 289, 15602-10, 2014) (Giuliani M M, *Proc Natl Acad Sci USA.*, 103, 10834-9, 2006). This example describes an approach utilizing fHbp-based cholera toxin holotoxin-like chimeras. This method uses the natural non-covalent assembly of antigens to the non-toxic cholera toxin B subunit (CTB) via the non-enzymatic cholera toxin A2 subunit (Hajishengallis G, *J Immunol.,* 154, 4322-32, 1995) (Jobling M G, *Infect Immun.,* 60, 4915-24, 1992). CTB is a strong adjuvant and CTB adjuvanticity can be enhanced if antigen and CTB are genetically fused (Stratmann, *Vaccines* (*Basel*), 3, 579-96, 2015). A dual promoter expression plasmid previously described was used, with one promoter controlling expression of fHbp inserted upstream and in-frame with the a2 subunit of cholera toxin, and the second promoter controlling expression of CTB. Both fHbp-A2 and CTB contained signal sequences for periplasmic export where non-covalent assembly of fHbp to CTB (fHbp-CTB) occurs as depicted in FIG. 1 (Price G A, *PLoS One.,* 7, e42434, 2012). fHbpR41S-CTB contains a mutation that markedly diminishes hfH binding to fHbp (Beernink P T, *J Immunol.,* 186, 3606-14, 2011).

Construction of Recombinant Protein Expression Plasmids

The expression plasmid used to create the fHbp holotoxin-like chimera was designated pGAP22 and is a derivative of a previously published dual promoter expression plasmid, pGAP22A2 (Price G A, *PLoS One.,* 7, e42434, 2012). Both pGAP22 and pGAP22A2 are identical in design and restriction sites, except pGAP22 contains a shortened A2 domain starting at amino acid 211 (Leu) of the cholera toxin A subunit (Zhang R G, *J Mol Biol.,* 251, 563-73, 1995). The fHbp gene was PCR amplified from genomic DNA obtained from MenB strain Cu385 (fHbp variant 1.1/subfamily B24) (Milagres L G, *Infect Immun.,* 66, 4755-61, 1998). The forward and reverse primers contained MscI and NotI restriction sites, respectively (Table 1). The forward primer started at amino acid 13 of the mature fHbp protein from *N. meningitidis* strain CU385 (subvariant 1.1 or B24) and the reverse primer started at the final amino acid of fHbp. The resultant PCR amplified fHbp gene was cloned into the MscI and NotI sites of pGAP22, which sandwiched it in-frame between the pelB leader sequence and the shortened a2 domain of cholera toxin. The new plasmid, pGAP22-fHbp, contained an IPTG-inducible T7 promoter controlling expression of the fHbp-a2 gene product, and an arabinose inducible promoter controlling the expression of the ctb gene product (Price G A, *PLoS One.,* 7, e42434, 2012).

TABLE 1

Primers used for making expression plasmids

| Primer | Sequence | SEQ ID NO: |
|---|---|---|
| fHbp-Forward-MscI | ACTTGGCCACAGGTGCGGGGC TTGCCGATGC | 4 |
| fHbp-Reverse-NotI | TTGCGGCCGCTTGCTTGGCGG CAAGGCCGATATG | 5 |
| fHbpR41S-mutation-For | GCTGGATCAGTCCGTCAGCAA AAACGAGAAACTGAAGCTGG | 6 |
| fHbpR41S-mutation-Rev | CCAGCTTCAGTTTCTCGTTTT TGCTGACGGACTGATCCAGC | 7 |
| fHbp-Forward-NdeI | ATCATATGGGTGCGGGGCTTG CCGATGC | 8 |
| fHbp-Reverse-XhoI | ATTCACTCGAGTTGCTTGGCG GCAAGGCCGATATG | 9 |

Construction of pGAP22-fHbpR41S Chimera

In order to create the fHbpR41S low hfH-binding mutant holotoxin-like chimeric protein, the QuikChange Lightning Site-Directed Mutagenesis Kit (Agilent Technologies) was used following the manufacturer's protocol. Mutagenic primers (Table 1) were used to mutagenize pGAP22-fHbp to create the new plasmid pGAP22-fHbpR41S. To make recombinant fHbp, the gene was PCR amplified from genomic Cu385 DNA as above and the gene product was inserted into the NdeI and XhoI restriction sites of the expression plasmid pET28 (EMD Millipore) and was in frame with both an N- and C-terminal 6-histidine tag. CTB was made using the CTB expression plasmid previously described (Price G A, *PLoS One.,* 7, e42434, 2012).

Protein Expression and Purification

All recombinant proteins were expressed under the same conditions but utilized different expression strains. Both the fHbp-CTB and fHbpR41S-CTB variants were expressed in BL21 STAR™ (DE3) (ThermoFisher), and CTB in BL21 (DE3). Recombinant fHbp was expressed in SHUFFLE EXPRESS® (DE3) (New England Biolabs). For protein expression, strains were grown in half-liter volumes in NZTCYM (1% NZ-amine, 1% tryptone, 0.5% NaCl, 0.5% yeast extract, 0.1% casamino acids, 0.2% MgSO4) pH 7.5 with 50 μg/mL of kanamycin. Cultures were grown at 37° C. and 250 rpm until they reached an $OD_{600}$ of approximately 3.0. The cultures were then grown at 16° C. and 250 rpm for approximately 30 minutes to acclimate to the new temperature then induced. For both the fHbp-CTB and fHbpR41S-CTB variants the cultures were induced with 0.1 mM IPTG and 0.1% arabinose. For both CTB and fHbp, expression was induced with 0.1 mM IPTG. After induction the cultures continued to incubate at 16° C. and 250 rpm for approximately 16-18 hours. Following expression, the bacteria were harvested by centrifugation and the pellets stored at −80° C. until use.

The primary and secondary purifications of all proteins were conducted under the same conditions. Primary purification was performed using Talon® metal affinity resin (Clonetech). Cell pellets were removed from −80° C. and suspended in 50 mM $NaH_2PO_4$+300 mM NaCl pH 8.0. Soluble extracts were obtained by the addition of ELUGENT™ detergent (EMD Millipore) to 2% final concentration, and RLYSOZYME™ together with Benzonase® following manufacturers' recommendations (EMD Millipore).

The cell extracts were incubated with mixing at room temperature for 15-30 minutes until lysates were no longer viscous. Insoluble debris was removed by centrifugation at 20,201×g for 10 minutes at 4° C. TALON® metal affinity resin was added to the soluble extract and mixed for 30 minutes at room temperature. The resin was then washed with 75-100 bed volumes of the above phosphate buffer. Proteins were then eluted with the above phosphate buffer containing 250 mM imidazole.

A secondary purification step using the multimodal anion exchange resin CAPTO™ Adhere (GE Healthcare) was conducted on all proteins to remove residual contaminants. Proteins were buffer exchanged into 20 mM Tris base pH 8.8 using ZEBA™ Spin desalting columns following the manufacturer's protocol (ThermoFisher). The proteins were then loaded onto a CAPTO™ Adhere column and eluted along a pH gradient with 20 mM Tris base pH 6.0. The purified proteins were dialyzed against 1×PBS pH 7.5 overnight at 4° C., then filter sterilized and stored at −80° C.

fHbp-CTB Chimeric Protein Immunogenicity

The present invention includes methods for using the chimeric fHbp proteins without the need for protein lipidation or exogenous adjuvants. Utilizing the holotoxin-like chimera approach, fHbp was effectively and non-covalently attached to CTB within the periplasm of E. coli. This allowed simple and efficient expression and purification of these chimeras. The data herein demonstrates that the WT fHbp-CTB chimera was able to bind to $G_{M1}$ ganglioside and serum hfH, suggesting that both the CTB and fHbp moieties were in a native-like conformation. In contrast, an fHbpR41S-CTB mutant chimera, while able to bind ganglioside, bound little hfH, demonstrating the expected effect of the fHbp mutation (Beernink, *J Immunol.,* 186, 3606-14, 2011). Both fHbp-CTB and fHbpR41S-CTB elicited similar anti-fHbp IgG levels and were significantly more immunogenic than fHbp alone or fHbp mixed with equimolar amounts of CTB. The improved immunogenicity of the fHbp-CTB chimeras compared to fHbp and fHbp+CTB is consistent with previous studies in which holotoxin-like chimeric proteins demonstrated enhanced antigen-specific IgG responses to conjugated antigens (Price G A, *PLoS One.,* 7, e42434, 2012) (Price G A, *PLoS Negl Trop Dis.,* 8, e3356, 2014). The anti-fHbp IgG levels elicited by both fHbp-CTB and fHbpR41S-CTB also resulted in higher bactericidal titers when tested in the hSBA assay compared to the titers elicited by fHbp admixed with CTB. When tested against strains that expressed the homologous fHbp, both chimeras elicited similar bactericidal titers. However against some strains expressing heterologous fHbp (1.4;B16 and 1.13;B09), the fHbp-CTB chimera elicited higher titers than fHbpR41S-CTB. The mutation from an R to S may have altered potentially cross-protective epitopes. An epitope mapping and crystal structure study of a bactericidal and hfH blocking anti-fHbp monoclonal antibody (12C1) demonstrated the R41 amino acid to be part of the antibody epitope, as well as one of the residues that make direct hydrogen bonds and/or salt bridges with 12C1 (Malito E, *Proc Natl Acad Sci USA,* 110, 3304-9, 2013). Although R41 mutational analysis was not provided, mutations in other residues that directly interacted with 12C1 demonstrated reduced binding of 12C1 to mutant versus wild-type fHbp proteins, and this binding was further reduced with multiple fHbp mutations (Malito E, *Proc Natl Acad Sci USA,* 110, 3304-9, 2013). Therefore, sequence variations among the subfamily B/variant 1 groups may have a greater additive effect on the bactericidal antibody cross protection if the original antigen already contains one mutation. hSBA of pooled sera was tested instead of individual mouse sera so individual hSBA variation within groups is not known. In addition, hSBA titers against heterologous strains may be enhanced by the combination of antibodies not present in any single serum (Beernink, *J Immunol.,* 186, 3606-14, 2011) (Costa, *MBio.,* 5, e01625-14, 2014).

Example 2

Mouse Immunizations and Blood Collection

Female BALB/c mice, 6-8 weeks old, were purchased from Charles River Labs and given food and water ad libitum. Groups of five mice were immunized IP three times at 14 day intervals (days 0, 14, and 28). The groups that were immunized with fHbp- or fHbpR41S-CTB chimeras were given 25 micrograms total protein/dose, and the other groups were immunized with equimolar amounts of antigen based on the amount given for the chimeras (see Table 2 for dosing). The molecular weights for all proteins were determined using the ExPASy Bioinformatics Resource Portal Compute pI/Mw tool (available online). The molecular weights for fHbp- and fHbpR41S-CTB chimeras were determined to be 87.8 kDa (fHbp-A2 29.8 kDa and CTB 58 kDa). The molecular weight for fHbp was calculated at 28.5 kDa. Blood was collected by submandibular bleeding using 4.5 mm Goldenrod Animal Lancets (Medipoint, Inc.) one day prior to primary immunization (day −1) and on day 21. The final bleed was performed on day 42 using cardiac puncture on anesthetized mice.

TABLE 2

Immunogenicity study design

| Group # | Immunizing Antigen* | Number of mice/group | Dose of antigen(s) (μg) |
|---|---|---|---|
| Group 1 | fHbp-CTB | 5 | 25 |
| Group 2 | fHbpR41S-CTB | 5 | 25 |
| Group 3 | fHbp + CTB | 5 | 8.1 + 16.5 |
| Group 4 | fHbp | 5 | 8.1 |
| Group 5 | CTB | 5 | 16.5 |
| Group 6 | PBS | 5 | None |

*Mice were immunized IP, three times at 14-day intervals $G_{M1}$ Ganglioside ELISAs To characterize the fHbp-CTB chimeras, a series of $G_{M1}$ ganglioside ELISAs were performed as previously described (Price G A, *PLoS One.,* 7, e42434, 2012). $G_{M1}$ ganglioside was diluted to 1 μg/mL in carbonate buffer and 100 microliters was added to each well. The plates were incubated at 4° C. overnight. Following coating, the plates were washed 2 times in wash buffer and 200 microliters of blocking buffer (1×PBS pH 7.5, 0.05% Tween 20, 5% normal horse serum) was added and incubated at 37° C. for one hour. Equimolar amounts of antigens were diluted in blocking buffer, added to each plate in duplicate, and serially diluted. For plates that were being evaluated for hfH binding, a fixed concentration of antigen was added to the appropriate wells. Plates were incubated at room temperature for one hour, and then washed 3× in wash buffer. A rabbit anti-cholera toxin antibody (Sigma Chemical Co.), or the monoclonal anti-fHbp antibody Jar 4 (National Institute for Biological Standards and Control) were used to probe for CTB or fHbp respectively, and 100 microliters of appropriately diluted antibody was added to each well and incubated at room temperature for one hour. Plates were washed again three times as above and either HRP-conjugated goat anti-rabbit or anti-mouse antibody was added and incubated for one hour at room temperature. The plates were then washed three times as above, OPD substrate was added, and plates were incubated in the dark for ~30 minutes. The reaction was stopped with 3M HCl and the optical densities were measured at 490 nm.

To measure hfH binding, human serum as a source of hfH was added to the appropriate wells of $G_{M1}$ ganglioside coated plates with either fHbp-CTB chimera bound as above. The human serum was serially diluted then incubated at room temperature for one hour. The plates were washed 3× as above and a mouse anti-human fH antibody (Sigma) was diluted in blocking buffer and added to each well (100 microliters). The plates were incubated for one hour at room temperature. Following incubation the plates were washed again three times as above and a horse radish peroxidase (HRP)-conjugated goat anti-mouse antibody was diluted in blocking buffer and added to each well. Plates were again incubated for one hour at room temperature then washed three times and developed with OPD substrate as above.

Quantitative ELISAs

Serum anti-fHbp and anti-CTB IgG levels were measured by quantitative ELISAs as previously described (Price, *PLoS One.*, 7, e42434, 2012) (Price, *PLoS Negl Trop Dis.*, 8, e3356, 2014). Murine anti-fHbp sera were quantitated against a calibrated mouse reference serum (Bethyl Laboratories). The reference serum was serially diluted and captured by Goat anti-mouse IgG (Bethyl Laboratories) coated at 1 µg/mL in carbonate buffer (0.015 M $Na_2CO_3$, 0.035M $NaHCO_3$, pH 9.5) to generate a reference curve. The sample wells were coated with recombinant fHbp or CTB diluted to 1 µg/mL in carbonate buffer. The 96-well plates were coated with 100 microliters of capture antibody or antigen and placed at 4° C. overnight. Following coating, the plates were washed two times (1×PBS pH 7.5+0.05% Tween 20) then blocked with 200 microliters of blocking buffer (1×PBS pH 7.5+0.05% Tween 20+1% Bovine Serum Albumin) for one hour at 37° C. After blocking, the blocking buffer was decanted and 100 microliters of fresh blocking buffer was added to each well. Reference serum or samples were diluted in blocking buffer, added (100 microliters) to the appropriate wells and serially diluted. The plates were then placed at 4° C. for overnight incubation. The plates were washed three times with the above wash buffer then 100 microliters of blocking buffer containing HRP-conjugated goat anti-mouse IgG was added and incubated at room temperature for 2-4 hours. The plates were then washed three times as above and 100 microliters of OPD substrate was added (Sigmafast™ OPD, Sigma Chemical Co.) and the plates were incubated for 15 minutes in the dark. To stop color development, 30 microliters of 3M HCl was then added to each well. The plates were then read at 490 nm using a microplate reader and the concentrations of the unknowns were interpolated from the standard curve.

Example 3

Human Serum Bactericidal Antibody Assay (hSBA)

The hSBA was performed based on the standardized protocol described previously (Borrow, *Clin Diagn Lab Immunol.*, 12, 970-6, 2005). Frozen stocks of MenB were plated onto BBL™ Columbia blood agar (CBA) plates with 5% sheep blood (Becton, Dickinson and Company) and incubated overnight at 37° C.+5% $CO_2$. A swath of colonies from the overnight plate were streaked onto a fresh CBA plate and incubated for 4 hours at 37° C.+5% $CO_2$. After incubation the bacteria were diluted into bactericidal buffer composed of Hank's balanced salt solution (HBSS; HYCLONE™) and 0.5% BSA (Amresco) and diluted to a final concentration of ~$5 \times 10^3$-$1 \times 10^4$ CFU/mL (50-100 CFU/10 µL). Heat inactivated pooled mouse sera were diluted 1/2 in bactericidal buffer (20 microliters final volume) and serially diluted in a sterile flat-bottomed 96 well plate (Costar). Ten microliters of the bacterial suspension followed by 10 microliters human complement (previously determined to be non-bactericidal against the test strain) were added to each well giving a final volume of 40 microliters (1/4-1/64 dilution of mouse sera). The plates were sealed and incubated at 37° C. with shaking at 65 rpm for one hour. Tryptic soy broth containing 1% Noble agar and cooled to 56° C. was added to each well (100 microliters) and allowed to harden. The plates were then incubated overnight at 37° C.+5% $CO_2$ and the following day colonies were enumerated using a dissecting microscope. The SBA titers were determined as the average of the highest reciprocal dilution that gave ≥50% reduction in colony forming units (CFU) compared to the average CFU of control wells that contained only active complement. Samples that had titers ≥64 were re-assayed using higher dilutions to determine the final titer.

Statistical Analysis

All statistical comparisons were performed using Graph-Pad Prism 6 software (La Jolla, Calif.). ANOVA was used to compare the differences in antibody amounts between immunization groups with the Tukey-Kramer post-test to determine statistical significance.

Example 4

Characterization of the fHbp-CTB and fHbpR41S-CTB Chimeras

Figure 2:
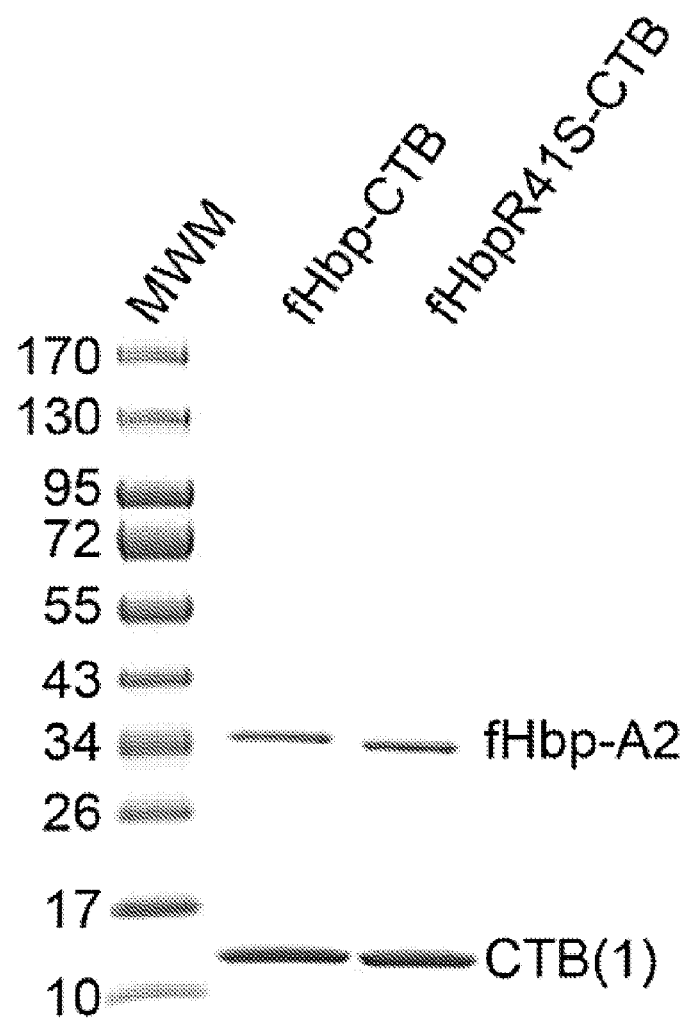

Both the fHbp-CTB and fHbpR41S-CTB chimeras were expressed in *E. coli* using a dual expression promoter plasmid similar to one previously described (Price, *PLoS One.*, 7, e42434, 2012). Both chimeras were purified using immobilized metal affinity chromatography (IMAC) followed by ion-exchange chromatography (IEX) to remove residual contaminating proteins and empty CTB from assembled fHbp-chimeras. FIG. 2 is an SDS-PAGE of both purified chimeras that had been reduced and heated. Under these conditions the CTB pentamer breaks down into monomers (~11.5 kDa) and separates from the fHbp-A2 portion (~30 kDa).

Figure 3A:
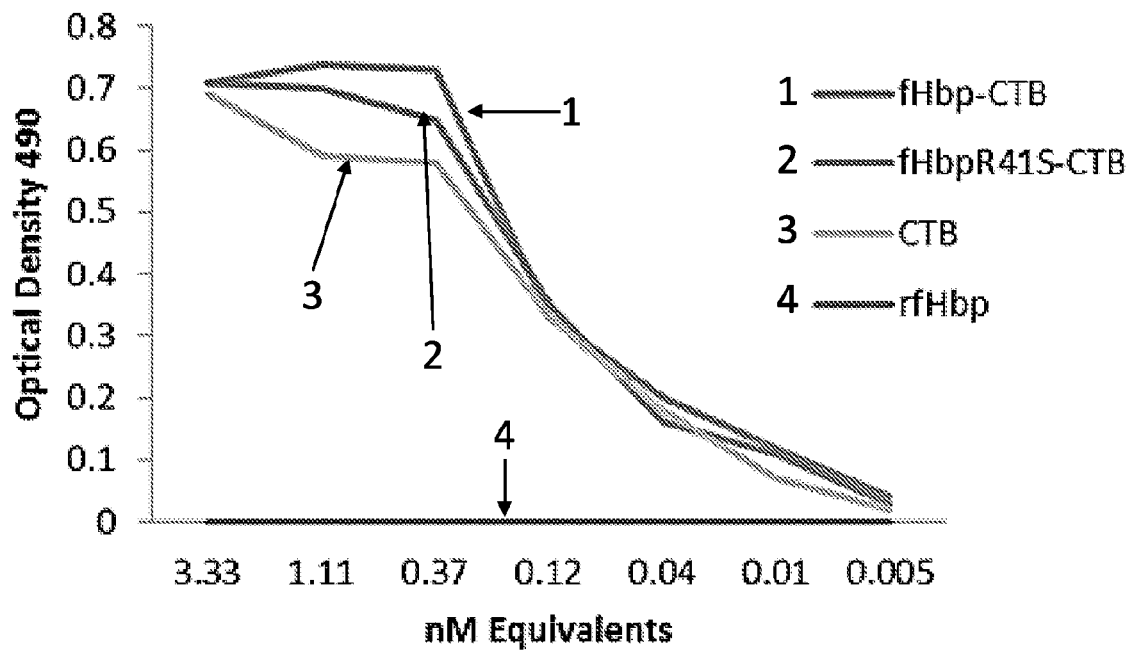
Figure 3B:
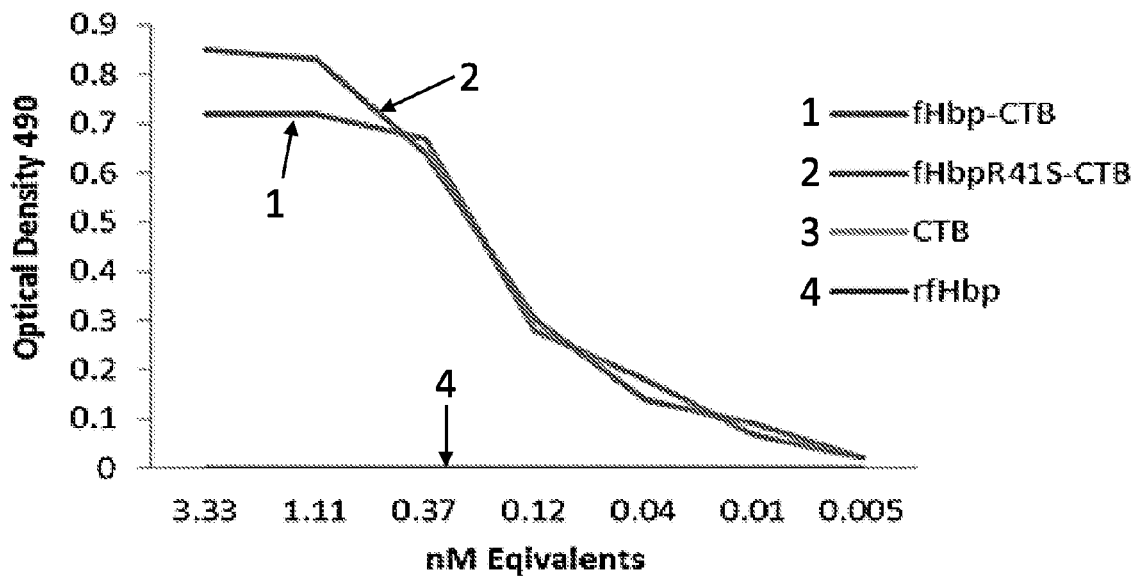

To characterize fHbp-chimera assembly and folding, a $G_{M1}$ ganglioside ELISA was performed, which exploits the ability of CTB to bind to solid-phase $G_{M1}$ ganglioside (Sack D A, *J Clin Microbiol.*, 11, 35-40, 1980). The WT- and R41S-CTB chimeras were compared to purified CTB in their ability to bind to $G_{M1}$ ganglioside. Using equimolar concentrations of antigens, both chimeras bound similarly to $G_{M1}$ ganglioside as CTB, demonstrating that the assembled fHbp did not perturb chimera $G_{M1}$ ganglioside binding (FIG. 3A). The anti-fHbp monoclonal antibody Jar4 was then used to demonstrate that fHbp-CTB and fHbpR41S-CTB were assembled with CTB and that the fHbp was in a native-like conformation (FIG. 3B) (Welsch J A, *J Infect Dis.*, 197, 1053-61, 2008). To further demonstrate native-like folding of fHbp in the context of the fHbp-CTB chimera, human serum was used as a source of fH to demonstrate fHbp-fH binding. Using a fixed concentration of chimera in the $G_{M1}$ ganglioside ELISA, human serum was added in two-fold dilutions and then the wells were probed with an anti-human factor H antibody. As can be seen in FIG. 3C, hfH bound to the fHbp-CTB chimera, whereas hfH binding to the fHbpR41S-CTB was greatly diminished, as has been demonstrated previously (Beernink, *J Immunol.*, 186, 3606-14, 2011). The data demonstrates proper fHbp-CTB chimera assembly without perturbation of $G_{M1}$ ganglioside binding, an important factor in the ability of CTB to behave as an immunostimulant (Francis M L, *J Immunol.*, 148, 1999-2005, 1992) (Nashar T O, *Proc Natl Acad Sci USA.*, 30, 226-30, 1996). The data also demonstrates that the fHbp moieties are functionally active, suggesting native-like conformation, an important aspect for the elicitation of bactericidal antibodies following immunization.

Immunogenicity of the fHbp-CTB and fHbpR41S-CTB Chimeras Following Intraperitoneal Immunization of BALB/c Mice Seven days after the second immunization (d21), both the WT and R41S fHbp-CTB chimeras elicited similar anti-fHbp IgG levels that were significantly higher than the fHbp responses measured in the fHbp+CTB and fHbp only immunization groups (FIG. 4A; $p<0.0001$). By day 42, 14 days following the third immunization, the anti-fHbp IgG antibody levels were significantly higher in the groups immunized with the fHbp-CTB chimeras than those measured on day 21 ($p<0.0001$). In addition to measuring the anti-fHbp IgG levels, anti-CTB IgG were also measured (FIG. 4B). Anti-CTB IgG concentrations were similar among all groups immunized with CTB regardless of whether fHbp was attached to CTB, demonstrating CTB in the form of the fHbp-CTB chimeras and CTB alone were equally immunogenic. These data demonstrate that CTB can act as a potent adjuvant for fHbp in the form of an assembled chimera, but not when admixed with fHbp.

Bactericidal Activity of Mouse Sera Using hSBA Assay

Figure 5:
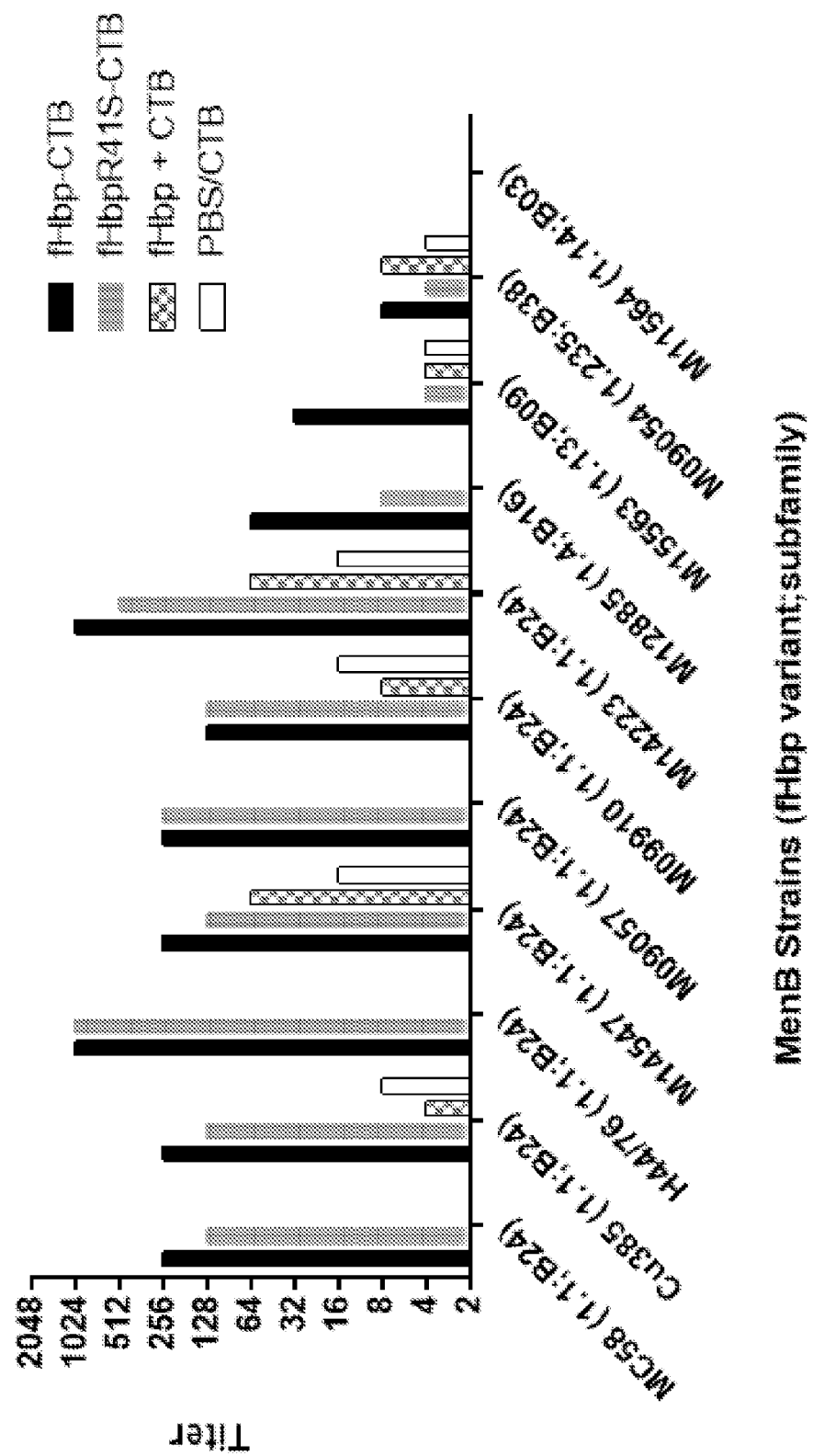

In order to determine whether the fHbp-CTB chimeras could elicit a bactericidal antibody response, hSBA titers of mouse sera pooled from each immunization group against a panel of strains expressing homologous or heterologous fHbp variants were determined. The panel consisted of laboratory strains as well as United States MenB disease isolates obtained from the Center for Disease Control and Prevention (CDC) (Table 3). As can be seen in FIG. 5, both the WT and R41S fHbp-CTB chimeras elicited strong bactericidal activity against all seven strains expressing the homologous fHbp variant (1.1; B24). The bactericidal activity of sera from the fHbp+CTB admixed group was more variable, with activity higher than background against two of the seven homologous fHbp strains. These strains were more sensitive to nonspecific bactericidal killing as demonstrated by the titers measured for sera from the PBS/CTB control groups. In all cases, bactericidal titers against the four CDC strains expressing heterologous fHbp variants were lower than against the homologous fHbp (1.1; B24) expressing strains. This is not without precedent as it has been previously demonstrated that immunization with fHbp (1.1; B24) elicited lower bactericidal titers against heterologous variant 1/subfamily B strains (Seib K L, *Infect Immun.*, 79, 970-81, 2011). Bactericidal titers measured against strains M12885 (1.4; B16) and M15563 (1.13; B09) were over four-fold higher in the WT fHbp-CTB versus the R41S fHbp-CTB immunized group. The two remaining strains M09054 (1.235; B38) and M11564 (1.14; B03) were relatively resistant to killing with sera from either fHbp-CTB or fHbpR41S-CTB immunized groups.

TABLE 3

MenB strains used for hSBA analysis including fHbp variant/subfamily type

| Lab Strains | Variant/Subfamily |
| --- | --- |
| MC58 | 1.1/B24 |
| Cu385 | 1.1/B24 |
| H44/76 | 1.1/B24 |

| CDC Strains | Variant/Subfamily |
| --- | --- |
| M14547 | 1.1/B24 |
| M09057 | 1.1/B24 |
| M09910 | 1.1/B24 |
| M14223 | 1.1/B24 |
| M12885 | 1.4//B16 |
| M15563 | 1.13/B09 |
| M09054 | 1.235/B38 |
| M11564 | 1.14/B03 |

Example 5

Immunogenicity Comparison of fHbp-CTB Holotoxin-Like Chimeric Proteins Versus the Commercial Vaccines Bexesero (4CMenB) and Trumenba (rLP2086)

Comparing the immunogenicity of the fHbp-CTB and the fHbpR41S-CTB chimeras, both were equally able to elicit anti-fHbp antibodies, and those antibodies were bactericidal against a number of subfamily B strains. These chimeric proteins were compared to the currently licensed serogroup B meningococcal vaccine. A second immunization study was set up using the fHbp-CTB chimera (Subfamily B24) that was described herein, and created a new fHbp-CTB chimera containing the subfamily A05 fHbp. The A05 subfamily chimera helped determine whether including both subfamily A and B chimeras in one immunization arm could elicit broader killing against strains expressing either the subfamily A or subfamily B fHbp. This is the rationale for the commercial vaccine Trumenba which contains one lipidated rfHbp from subfamily A and one from subfamily B.

The study design table below lists the different immunization groups, the immunizing antigen, the number of mice per group, and the dose of antigen given. Some groups contained aluminum salts as an adjuvant to determine what effect it would have on the overall immunogenicity of the antigens. The two commercial vaccines, TRUMENBA® (rLP2086) and BEXSERO® (4CMenB) were used to compare the immunogenicity of the vaccine disclosed herein with those on the market. BALB/c mice were immunized three times at 14-day intervals. Immunizations were delivered intraperitoneally. Blood was collected on days −1, −21, and −42. The sera was used to measure fHbp-specific antibody amounts and group sera was pooled to test for bactericidal activity against a number of subfamily B and subfamily A strains using the humans serum bacterial assay (hSBA).

Study Design Table

| Group # | Immunizing Antigen | Mice/group | Dose of antigen(s) [µg] |
|---|---|---|---|
| Group 1 | fHbp(B24)-CTB | 5 | 24 |
| Group 2 | fHbp(B24 + A05)-CTB | 5 | 12 + 12 |
| Group 3 | fHbp(B24 + A05)-CTB + $Al^{3+}$ | 5 | 12 + 12 ($Al^{3+}$ 0.05 mg) |
| Group 4 | rfHbp (B24 + A05) | 5 | Equimolar to chimera |
| Group 5 | rfHbp (B24 + A05) + CTB | 5 | Equimolar to chimera |
| Group 6 | rfHbp (B24 + A05) + $Al^{3+}$ | 5 | Equimolar to chimera + ($Al^{3+}$ 0.05 mg) |
| Group 7 | CTB | 5 | Equimolar to chimera |
| Group 8 | rLP2086 (B01 + A05) | 5 | 1/5 human dose (12 + 12) |
| Group 9 | 4CMenB (B24) | 5 | 1/5 human dose (10) |
| Group 10 | PBS + $Al^{3+}$ | 5 | $Al^{3+}$ 0.05 mg + PBS only |

Example 7

Method of Administration Combining Chimeric fHbps

Figure 6:
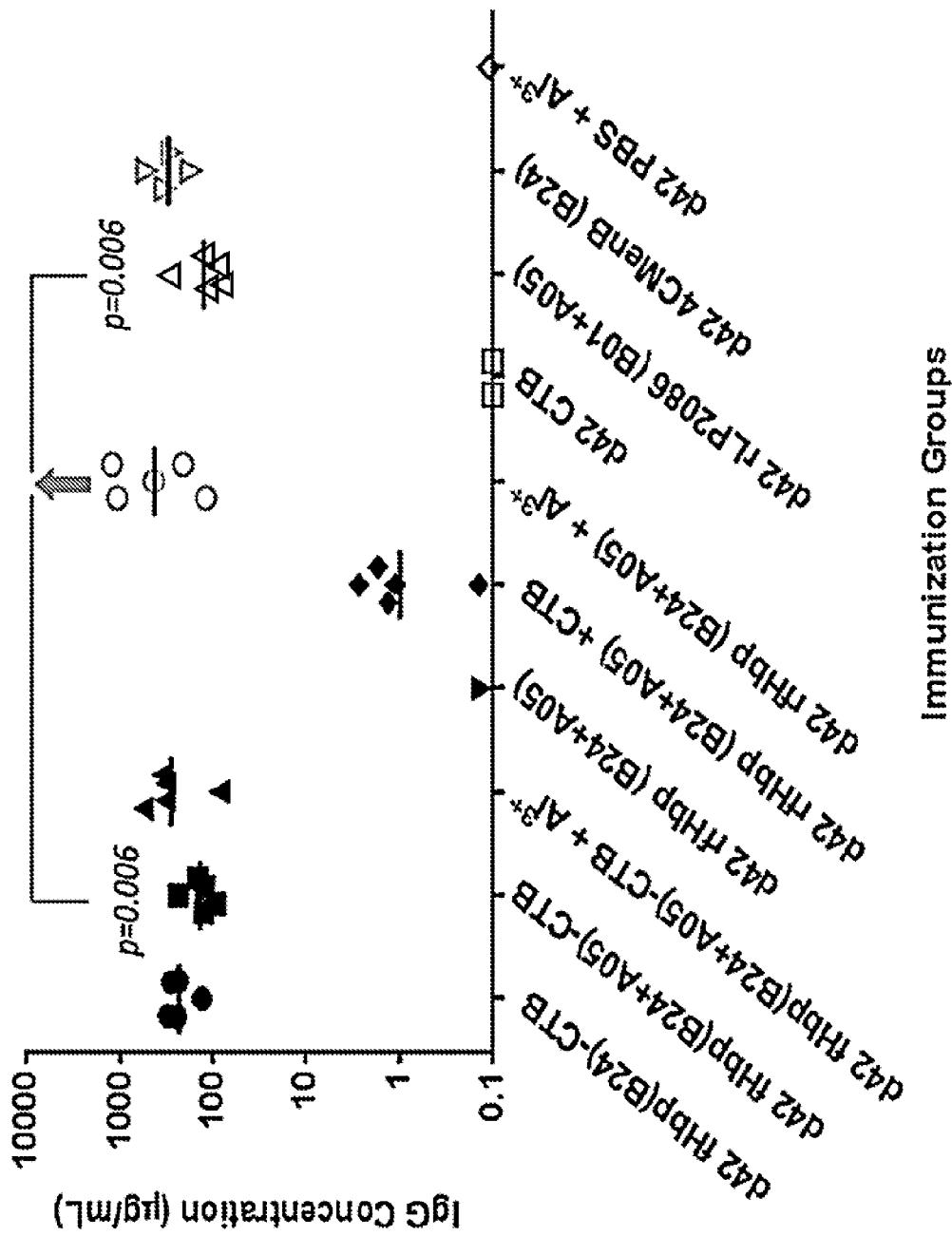

FIG. 6 is a graph of day 42 (d42) anti-fHbp IgG amounts measured against fHbp B24 antigen. The highest geometric mean titers were measured in the group immunized with both the B24 and A05 recombinant fHbp protein using aluminum salt as an adjuvant. These levels were significantly higher than the group immunized with both the A and B subfamily fHbp-CTB chimeras and the Trumenba (rLP2086) group. It should be noted that the fHbp B subfamily protein in Trumenba is B01 and not B24 which was used as the coating antigen for these ELISAs. It is likely the lower levels of antibodies were the result of sequence variation between B24 and B01. BEXSERO® (4CMenB) contains the B24 fHbp antigen.

Figure 7:
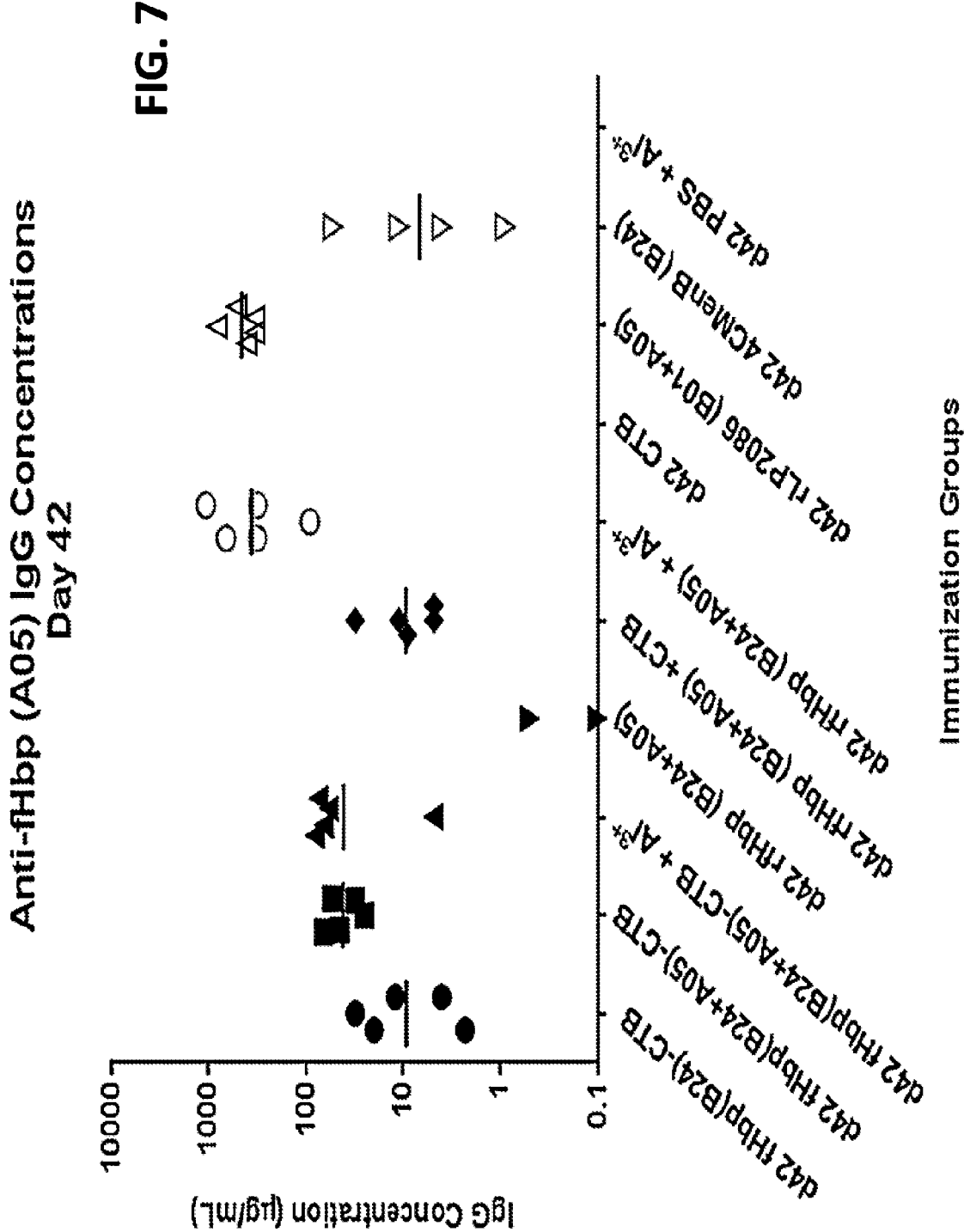

FIG. 7 is a graph of day 42 anti-fHbp IgG amounts against fHbp subfamily A05 as measured by quantitative ELISA. The highest geometric mean titers against fHbp A05 were measured in the groups immunized with both the B24 and A05 recombinant fHbps adjuvanted with aluminum salts and Trumenba (rLP2086). These two groups had significantly higher anti-fHbp A05 antibody amounts compared to all the other groups. The A05 fHbp-CTB chimera did not elicit high titers and was not much higher than background as compared to the group immunized with the B24 fHbp-CTB chimera. The addition of aluminum salt did not significantly improve the immunogenicity of the A05 fHbp-CTB chimera.

Bactericidal Activity of Pooled Mouse Sera Using the Human Serum Bactericidal Assay (hSBA)

Figure 8:
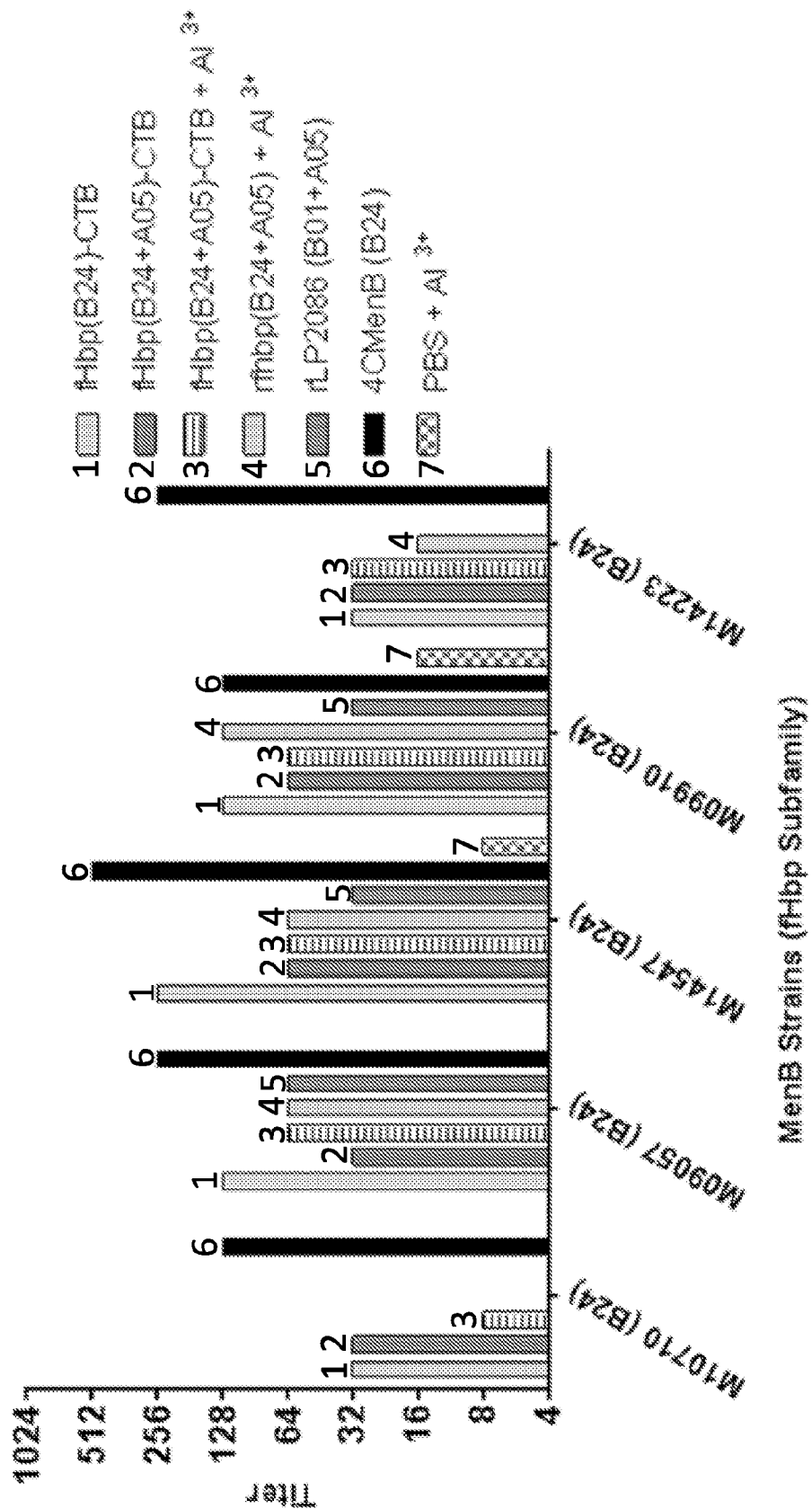

FIG. 8 is a figure of the bactericidal activity of pooled mouse sera against 5×B24 meningococcal strains. These 5 strains express fHbp that is identical to the fHbp-CTB chimeras and the fHbp in the commercial vaccine Bexsero (4CMenB). All groups immunized with fHbp-CTB without aluminum salt adjuvant elicited ≥4-fold rise in bactericidal titers against all strains tested. The recombinant fHbp vaccine containing aluminum salts as an adjuvant elicited the highest anti-fHbp IgG titers but was no more effective than the fHbp-CTB vaccines and elicited ≥4-fold titers in 3 of the 5 strains (minimum limit of detection was a titer of 8). Furthermore, one strain demonstrated no bactericidal killing with this vaccine. The commercial vaccine Bexsero (4CMenB) was the most active of the vaccines eliciting the highest titers. However, Bexsero is a 4-component vaccine and has 3 additional antigen targets besides fHbp. The other commercial vaccine, Trumenba (rLP2086) contained a heterologous subfamily B fHbp (B01) and elicited ≥4-fold titers against 3 of the 5 strains.

Figure 9:
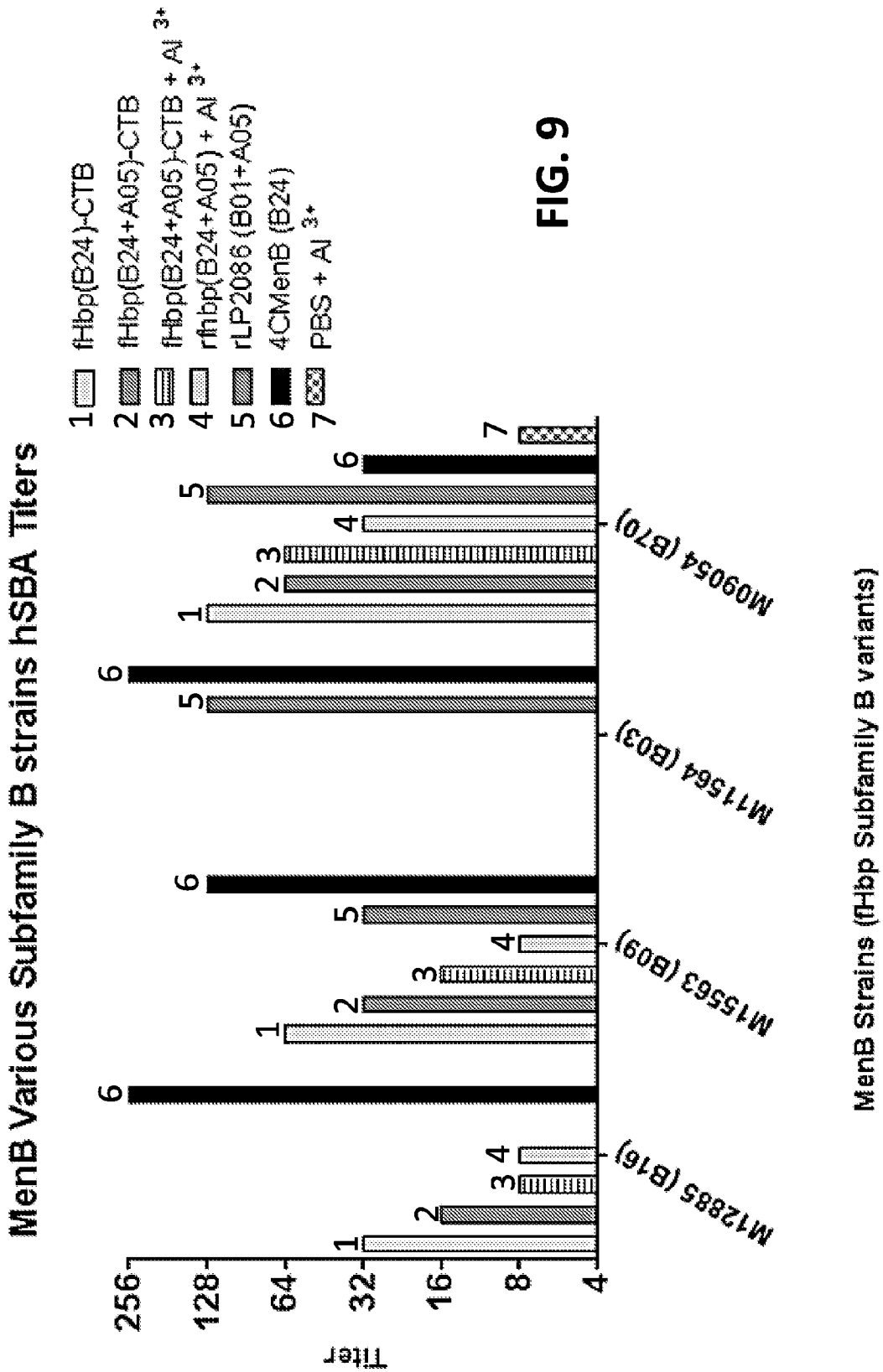

FIG. 9 is a figure of the bactericidal activity of pooled mouse sera against 4 various fHbp subfamily B expressing meningococcal strains. The fHbp-CTB chimeras were bactericidal against 3 of the 4 strains with various levels of bactericidal activity. The fHbp-CTB chimeras elicited higher bactericidal activity compared to the group immunized with rfHbp and aluminum salt as an adjuvant. The commercial vaccine BEXSERO® was the only vaccine that was bactericidal against all 4 strains. Trumenba (rLP2086) was bactericidal against 3 of the 4 strains.

Figure 10:
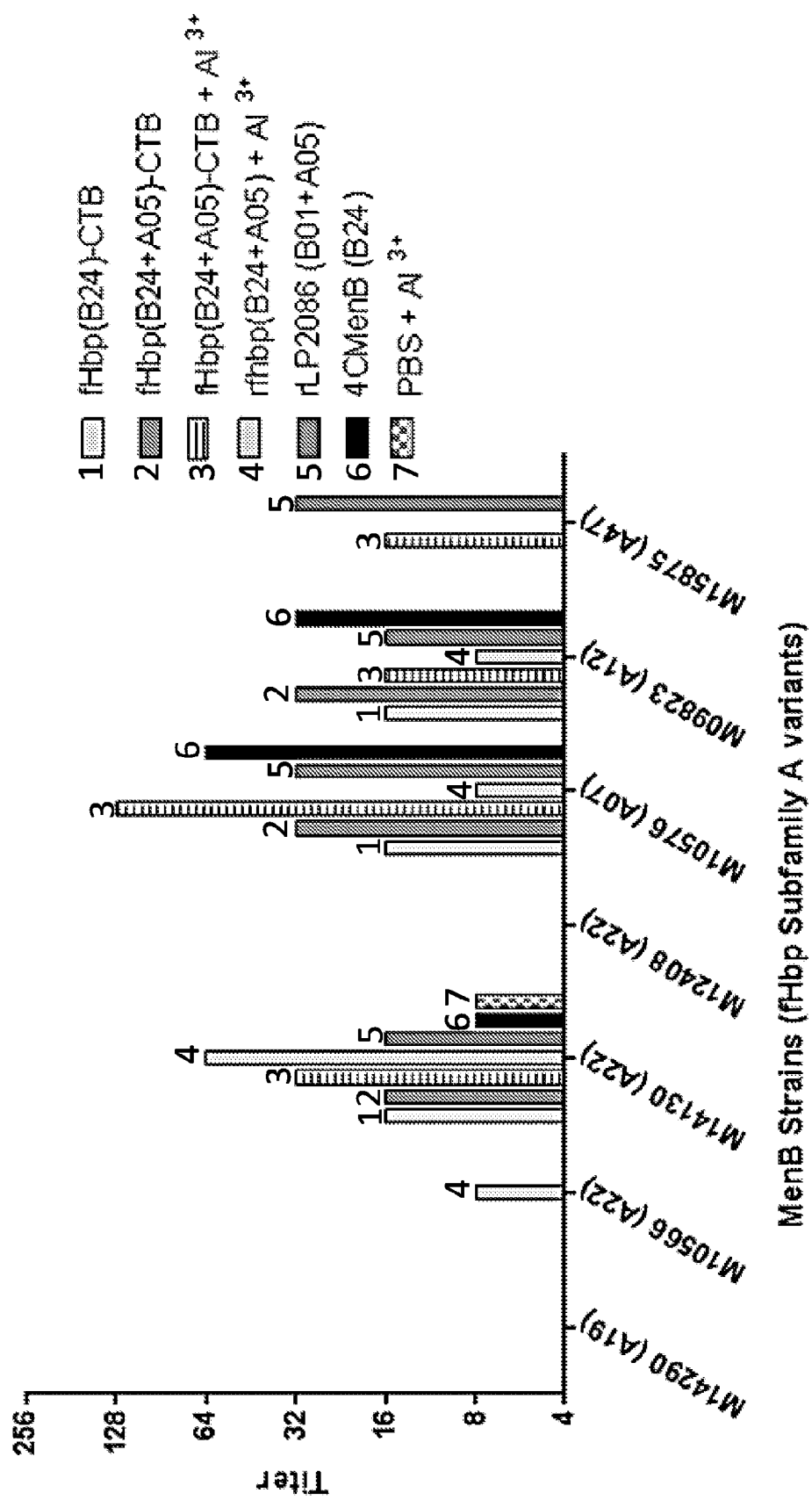
Figure 11:
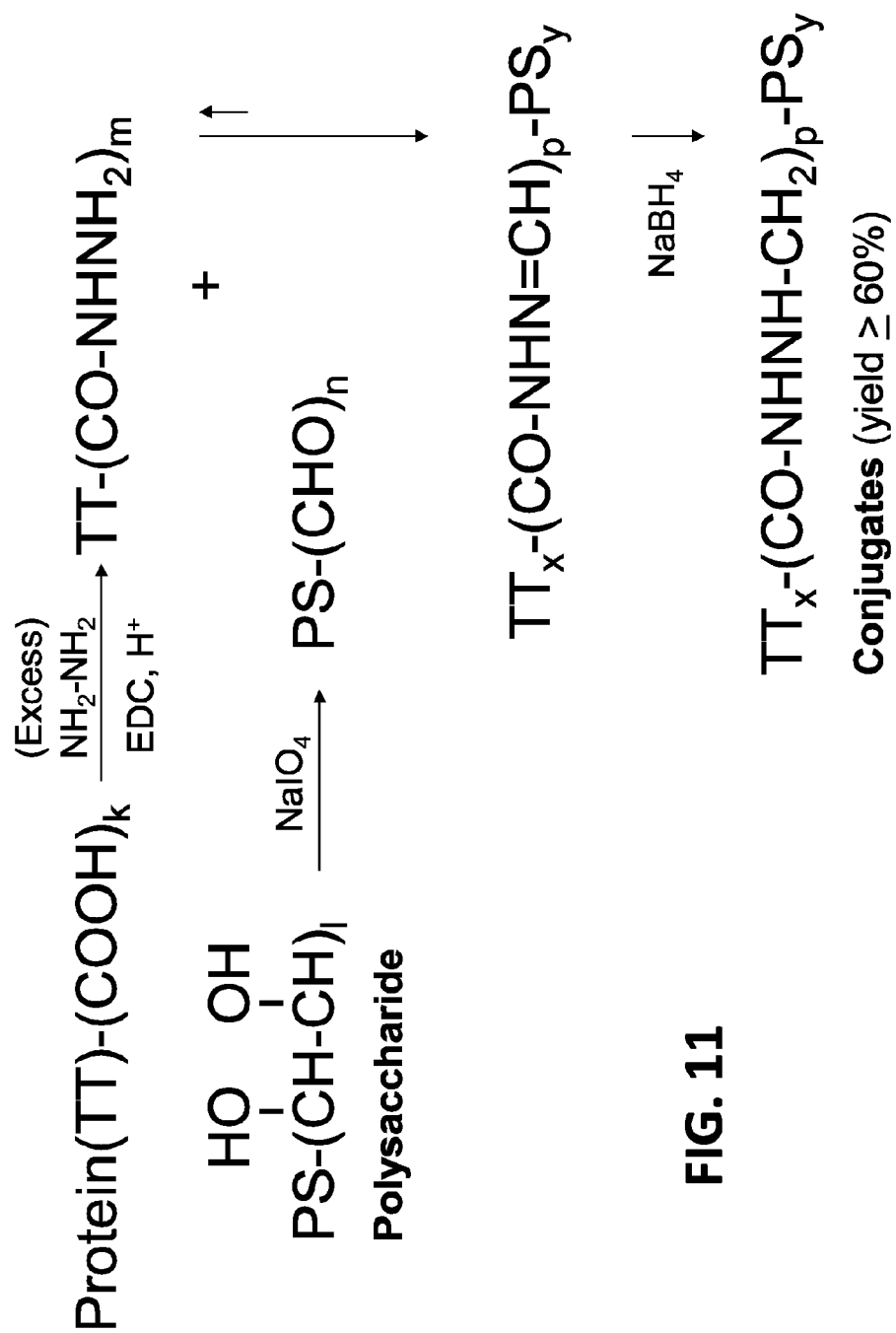

FIG. 10 shows the bactericidal activity of pooled mouse sera against 7 various fHbp subfamily A expressing meningococcal strains. Two of the seven strains were resistant to killing against all sera tested. The fHbp-CTB chimeras elicited bactericidal activity against 4 of the 7 strains depending on vaccine preparation. This was a very good result, considering anti-fHbp subfamily A IgG levels were significantly lower compared to the group with rfHbp mixed with aluminum salt as an adjuvant and TRUMENBA® (rLP2086). Although these two vaccines had the highest anti-fHbp subfamily A antibody titers, this did not translate in to markedly better bactericidal titers. BEXSERO® was bactericidal against all subfamily B strains but elicited less bactericidal activity against the subfamily A strains (3 of 7).

Example 8

Conjugation of Meningococcal Serogroup A Polysaccharide to an fHbp-CTB Holotoxin-Like Chimera for the Development of Multivalent Meningococcal Vaccines Meningococcal serogroup A polysaccharide (MAP) was chemically conjugated to the fHbp-CTB holotoxin-like chimera, CTB, fHbp, and fHbp with CTB using the conjugation methods, reductive amination (Lee C H, *Vaccine,* 27, 726-32, 2009, incorporated by reference) (FIG. 11). An immunogenicity study was conducted in mice to determine whether the fHbp-CTB chimera could serve as an effective carrier molecule and retain fHbp immunogenicity to elicit antibodies to MAP and fHbp, thereby creating a conjugate vaccine with valency to other meningococcal serogroups. MAP was conjugated to CTB and fHbp alone, and in mixtures, to determine whether the use of the fHbp-CTB holotoxin-like chimera was superior to either antigen alone or mixed as carriers. The study design is as follows in Table 4 below:

TABLE 4

| fHbp-CTB-MAP Immunogenicity study design | | | |
|---|---|---|---|
| Group # | Immunizing Antigen | Mice/group | Dose of antigen(s) (μg) |
| Group 1 | fHbp-CTB-MAP | 10 | 1 |
| Group 2 | fHbp/CTB-MAP | 10 | 1 |
| Group 3 | fHbp-H + CTB-H-MAP | 10 | 1 |

TABLE 4-continued fHbp-CTB-MAP Immunogenicity study design

| Group # | Immunizing Antigen | Mice/group | Dose of antigen(s) (µg) |
|---|---|---|---|
| Group 4 | fHbp-MAP 1/3 + CTB-MAP 2/3 | 10 | 1 |
| Group 5 | TT-MAP | 10 | 1 |
| Group 6 | MAP | 10 | 1 |
| Group 7 | fHbp-CTB | 10 | 1 |
| Group 8 | fHbp-MAP | 10 | 1 |
| Group 9 | CTB-MAP | 10 | 1 |

Group 1 consists of MAP chemically conjugated to the fHbp-CTB chimera. Group 2 consists of fHbp and CTB mixed together and activated with hydrazide groups then chemically conjugated to MAP (Lee C H, Vaccine, 27, 726-32, 2009). Group 3 consists of fHbp and CTB that were activated with hydrazide groups separately then mixed together with MAP for conjugation. Group 4 was a mixture of fHbp and CTB conjugated to MAP alone then mixed at ⅓ (fHbp-MAP) and ⅔ (CTB-MAP) amounts, which was equimolar to the fHbp-CTB chimera group. Group 5 was immunized with tetanus toxoid (TT)-MAP conjugate which has been demonstrated to elicit strong anti-MenA bactericidal antibodies in mice (Lee C H, Vaccine, 27, 726-32, 2009). Group 6 was immunized with MAP alone which served as a negative control since MAP alone is poorly immunogenic in mice (Lee C H, Vaccine, 27, 726-32, 2009). Group 7 was immunized with the fHbp-CTB chimera alone (no MAP conjugation), and Groups 8 and 9 were immunized with fHbp-MAP or CTB-MAP, respectively. All mice were immunized with 1 µg of protein subcutaneously three times at 14 day intervals. Blood was collected at day 26 and 42.

Quantitative ELISAs of Day 26 Sera

Figure 12A:
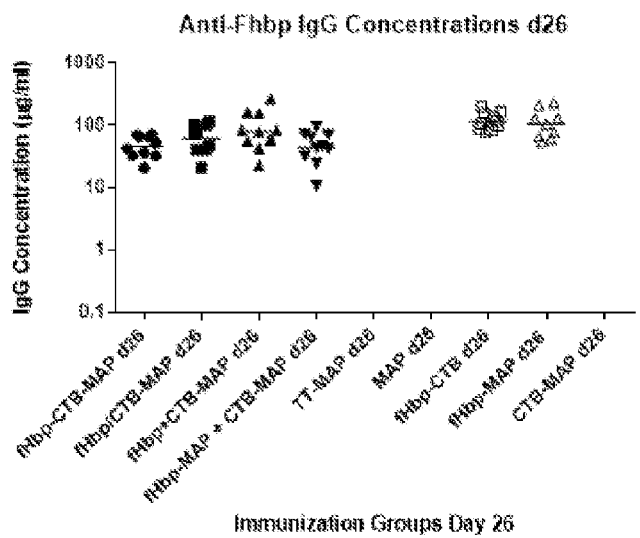
Figure 12B:
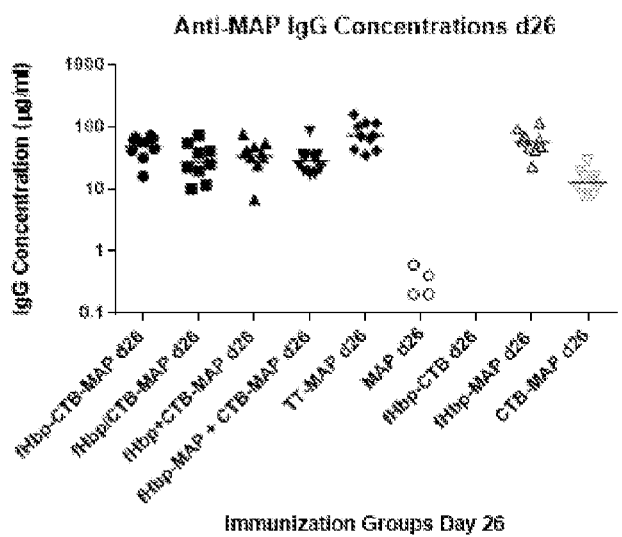
Figure 12C:
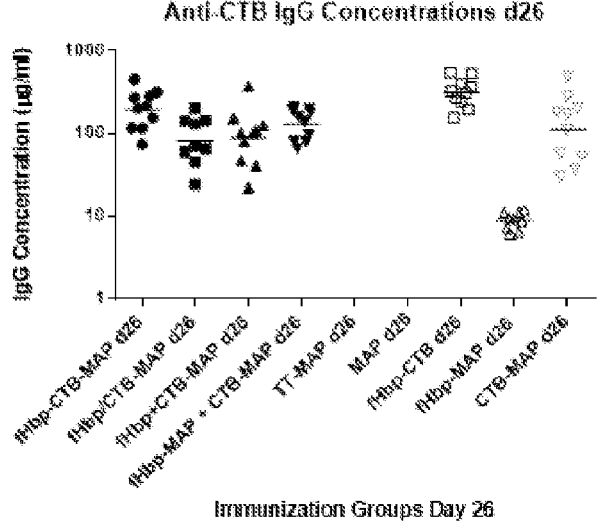

Quantitative ELISAs were performed on day 26 sera (12 days following the second dose of antigen) to test the sera for antibodies against fHbp, CTB, and MAP. The results are presented in FIGS. 12A-12C and show individual mouse antibody concentrations and the geometric mean concentration of each group (straight line). In FIG. 12A, individual serum samples were measured for antibodies against fHbp. The groups immunized with the chimera alone (Group 7) and fHbp-MAP (Group 8) had the highest geometric mean antibody amounts which were significantly higher than the fHbp-CTB-MAP and fHbp-MAP+CTB-MAP immunized groups (Groups 1 and 4, respectively; P<0.05). FIG. 12B demonstrates the anti-MAP IgG concentrations for each mouse at day 26. The group immunized with TT-MenA (Group 5) had the highest geometric mean anti-MAP antibody amounts compared to the other groups but only reached significance against the CTB-MAP group which had the lowest antibody amounts amount the conjugates (Group 9; P<0.05). MAP alone was poorly immunogenic, demonstrating each conjugate helped to improve MAP immunogenicity. FIG. 12C demonstrates the antibody response to CTB. The group immunized with fHbp-MAP alone had background antibodies to CTB. This suggests low-level contamination of this group with CTB, which may have acted as an adjuvant as this group had the highest anti-fHbp IgG antibody amounts of all the MAP conjugates.

Quantitative ELISAs of Day 42 Sera

Figure 13B:
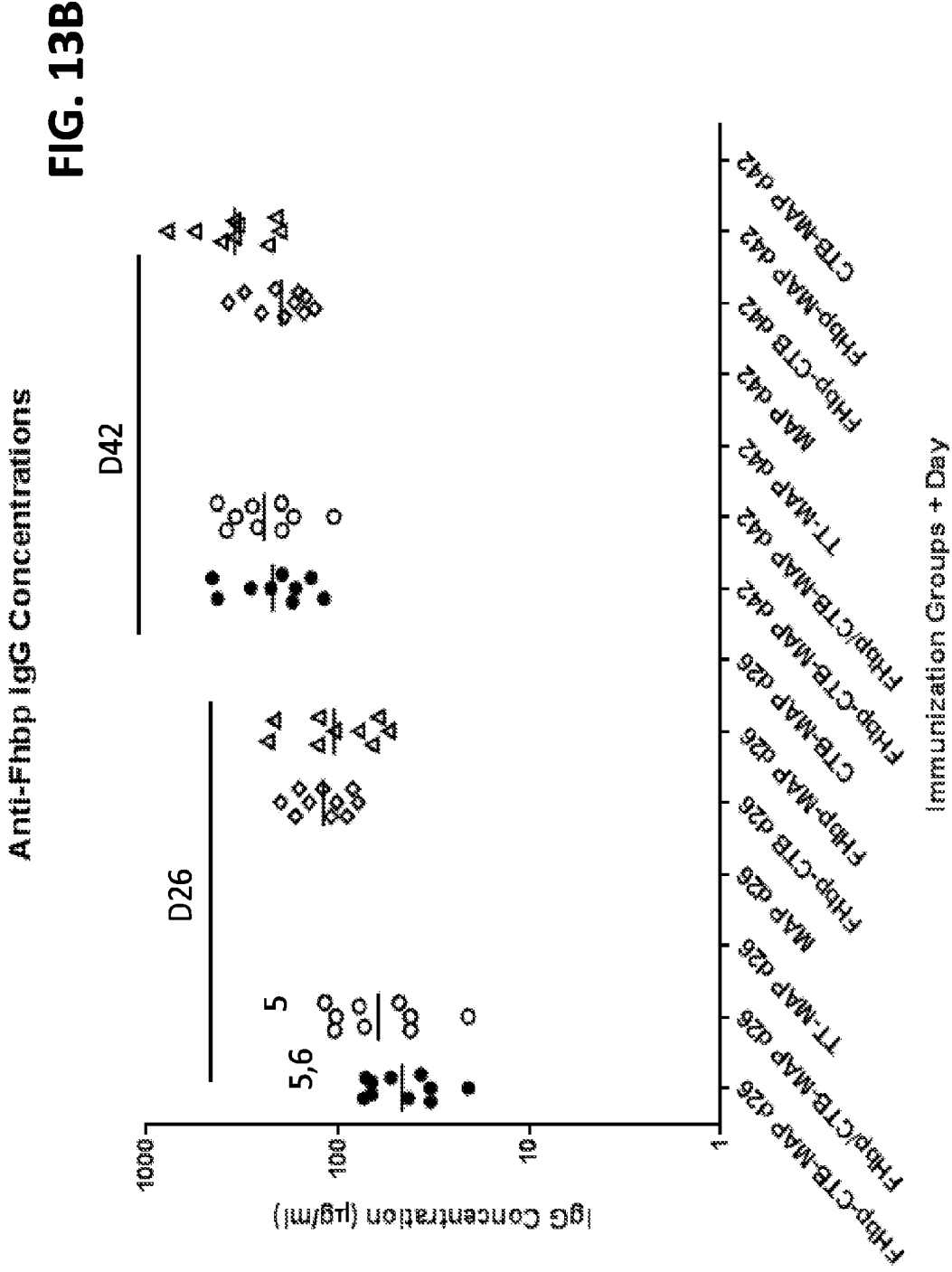

Following the third dose (day 42 sera), FHbp, CBT or FHbp-A2-CTB functioned as suitable carrier proteins for stimulating anti-MAP antibodies (FIG. 13A). FHbp chimeras and recombinant FHbp whether conjugated to MAP or not stimulated similar anti FHbp IgG concentrations at day 42 (FIG. 13B).

Human Serum Bactericidal Activity Assays of Day 42 Serum Samples

Figure 14A:
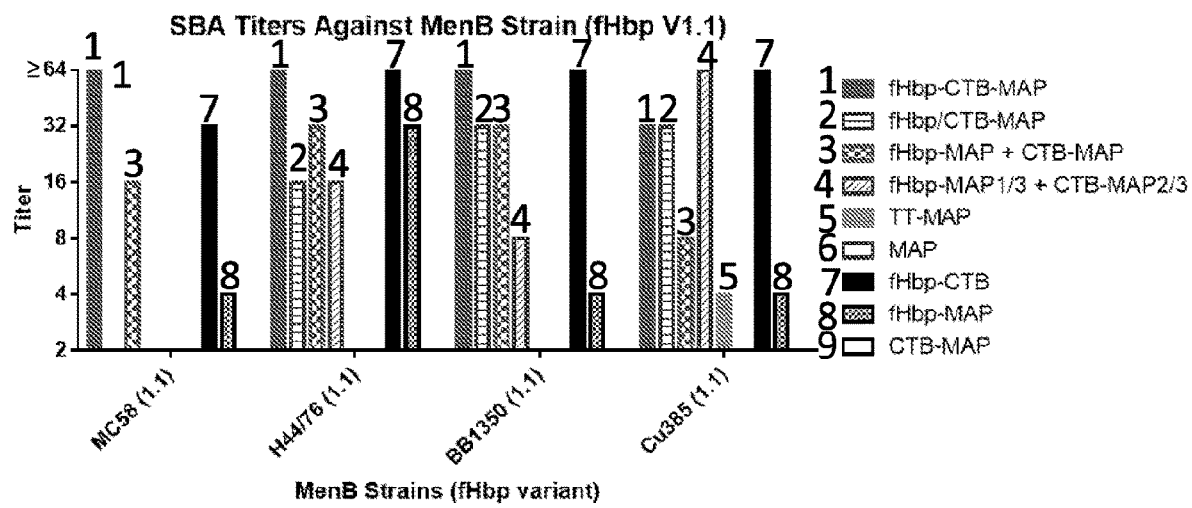

Four serogroup B meningococcal (MenB) strains expressing homologous fHbp (variant 1.1) were used to measure bactericidal activity of day 42 pooled immune sera. Human IgG depleted plasma was used as a complement source (Brookes, J Immunol Methods, 391, 39-49, 2013). In FIG. 14A, both the fHbp-CTB-MAP conjugate and fHbp-CTB chimera elicited the highest bactericidal titers against all 4 MenB strains. The groups immunized with fHbp and CTB mixed had more variable titers depending on the strain. The group immunized with fHbp-MAP, which had the highest anti-fHbp IgG antibody amounts at day 42 (FIG. 13B) had the poorest bactericidal titers among the other immunization groups which contained fHbp. This suggests that the majority of anti-fHbp antibodies elicited following fHbp-MAP immunization were non-bactericidal in nature or recognized non-functional epitopes as the result of chemical conjugation to MAP.

Figure 14B:
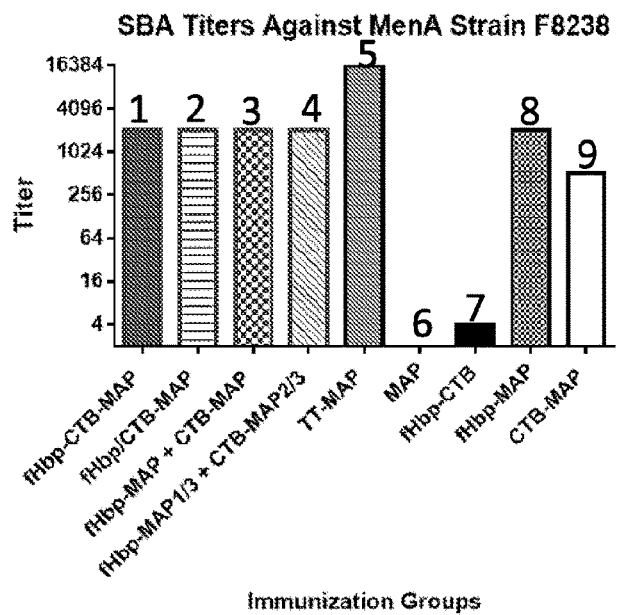

To perform hSBA assays against MenA, a normal pooled human complement source with no intrinsic ability to kill the MenA strain was used as previously described (Price G A, Clin Vaccine Immunol., 22, 1227-34, 2015). The group immunized with TT-MAP elicited the highest bactericidal titers compared to all other groups (FIG. 14B). This was also the group that had the highest anti-MAP antibodies as demonstrated in FIG. 13A. In terms of anti-MenA bactericidal titers, the remaining conjugates all elicited the same MenA titers regardless of the conjugated protein, except for CTB-MAP. CTB-MAP was also the group that elicited the lowest anti-MAP antibodies as demonstrated in FIG. 13A. Group 7 (fHbp-CTB) had a low titer to the MenA strain. It is possible that the anti-fHbp antibodies elicited following vaccination may have had some bactericidal activity against the MenA test strain (FIG. 14B).

Results

Serogroup A meningococcal conjugate vaccines using FHbp, CBT or FHbp-A2-CTB as immunogenic carrier proteins were tested in the mouse immunogenicity study. Bactericidal anti-FHbp immune responses were diminished when recombinant FHbp was the carrier, but were preserved when MenA PS was conjugated to FHbp-A2-CTB chimeras (FIG. 14A). The MenA-FHbp-A2-CTB conjugate elicited a strong anti-MenA bactericidal antibody response (hSBA 1:2048), as did CTB-MenA and FHbp-MenA conjugates, but less than MenA-TT (hSBA 1:16384). Antibodies induced by these vaccines were tested against MenB strains expressing FHbp subfamily B24 (FIG. 14A). MenA-FHbp-A2-CTB hSBA titers were similar to those induced by the FHbp-A2-CTB chimera alone, and over 16-fold higher than those of the MenA-FHbp conjugate group.

This study shows improved preservation of the FHbp antigen in a MenA glycoconjugate when FHbp expressed as a cholera holotoxin-like chimera is used as the carrier protein.

We claim:

1. An immunogenic composition, comprising a bacterial capsular polysaccharide conjugated to a protein, wherein the protein comprises:

a *N. meningitidis* factor H binding protein (fHbp) fused to a linking domain; and a cholera toxin subunit B (CTB), wherein the fHbp is covalently or non-covalently linked to the CTB, wherein the capsular polysaccharide comprises a *N. meningitidis* serogroup A, serogroup B, serogroup C, serogroup D, serogroup X, serogroup Y, serogroup Z, serogroup 29E or serogroup W capsular polysaccharide.

2. The immunogenic composition of claim 1, wherein the capsular polysaccharide is a *N. meningitidis* serogroup A capsular polysaccharide.

3. The immunogenic composition of claim 1, wherein the fHbp-linking domain is non-covalently linked to CTB.

4. The immunogenic composition of claim 1, wherein the amino acid sequence of the fHbp is at least 95% identical to SEQ ID NO: 1.

5. The immunogenic composition of claim 4, wherein the amino acid sequence of the fHbp comprises SEQ ID NO: 1.

6. The immunogenic composition of claim 1, wherein the linking domain comprises a cholera toxin subunit A2 domain.

7. The immunogenic composition of claim 6, wherein the amino acid sequence of the A2 domain is at least 95% identical to SEQ ID NO: 2.

8. The immunogenic composition of claim 7, wherein the amino acid sequence of the A2 domain comprises or consists of SEQ ID NO: 2.

9. The immunogenic composition of claim 1, wherein the amino acid sequence of the CTB is at least 95% identical to SEQ ID NO: 3.

10. The immunogenic composition of claim 9, wherein the amino acid sequence of the CTB comprises or consists of SEQ ID NO: 3.

11. The immunogenic composition of claim 1, further comprising a pharmaceutically acceptable carrier.

12. The immunogenic composition of claim 11, further comprising an adjuvant.

13. A method of inducing an immune response to *N. meningitidis* in a subject, comprising administering to the subject an effective amount of the immunogenic composition of claim 1, thereby inducing the immune response to the bacterium.

14. The method of claim 13, wherein the immune response is a protective immune response, and wherein the capsular polysaccharide is a *N. meningitidis* serogroup A capsular polysaccharide.

15. The method of claim 13, wherein the immune response is a therapeutic response, and wherein the capsular polysaccharide is a *N. meningitidis* serogroup A capsular polysaccharide.

16. The method of claim 13, wherein the subject is human.

* * * * *